United States Patent
Ishimaru

(10) Patent No.: US 12,102,430 B2
(45) Date of Patent: Oct. 1, 2024

(54) SPECTRAL MEASUREMENT DEVICE AND SPECTRAL MEASUREMENT METHOD

(71) Applicant: NATIONAL UNIVERSITY CORPORATION KAGAWA UNIVERSITY, Takamatsu (JP)

(72) Inventor: Ichiro Ishimaru, Takamatsu (JP)

(73) Assignee: NATIONAL UNIVERSITY CORPORATION KAGAWA UNIVERSITY, Takamatsu (JP)

( * ) Notice: Subject to any disclaimer, the term of this patent is extended or adjusted under 35 U.S.C. 154(b) by 0 days.

(21) Appl. No.: 18/285,763

(22) PCT Filed: Mar. 30, 2022

(86) PCT No.: PCT/JP2022/016340
§ 371 (c)(1),
(2) Date: Oct. 5, 2023

(87) PCT Pub. No.: WO2022/220145
PCT Pub. Date: Oct. 20, 2022

(65) Prior Publication Data
US 2024/0268719 A1  Aug. 15, 2024

(30) Foreign Application Priority Data
Apr. 13, 2021 (JP) .................. 2021-067907

(51) Int. Cl.
*A61B 5/1455* (2006.01)
*A61B 5/145* (2006.01)

(52) U.S. Cl.
CPC ........ *A61B 5/1455* (2013.01); *A61B 5/14532* (2013.01)

(58) Field of Classification Search
CPC ..... A61B 5/004; A61B 5/0075; A61B 5/0205; A61B 5/1455; A61B 5/14551; A61B 5/14552; A61B 5/14532
See application file for complete search history.

(56) References Cited

U.S. PATENT DOCUMENTS 5,900,632 A * 5/1999 Sterling ............. A61B 5/14532
250/252.1
2017/0014056 A1 * 1/2017 Newberry ............ A61B 5/1455
(Continued)

FOREIGN PATENT DOCUMENTS

JP  2006-201975 A  8/2006
JP  2014-008139 A  1/2014
(Continued)

OTHER PUBLICATIONS

Kosuke Nogo et al.; "Infrared Emission Spectroscopic Imaging of Microplastics Using Long-Wavelength Infrared Hyperspectral Camera With Imaging-Type Two-Dimensional Fourier Spectroscopy;" 2021 11th Workshop on Hyperspectral Imaging and Signal Processing; Evolution in Remote Sensing (WHISPERS).
(Continued)

*Primary Examiner* — Chu Chuan Liu
(74) *Attorney, Agent, or Firm* — Oliff PLC

(57) ABSTRACT

A spectral measurement device to detect measurement light including light emitted from a measurement object and to measure spectral characteristic of the light, including: a spectral optical system to disperse the measurement light; a detection unit to detect intensity of light dispersed by the spectral optical system; a spectral characteristic acquisition unit to acquire a measurement light spectral characteristic indicating a relationship between a light intensity and a wavelength of the measurement light on a basis of a detection result; a storage unit to store spectral characteristic information on possible background light, the information
(Continued)

indicating a spectral characteristic of the possible background light, which involves a spectral sensitivity characteristic of the detection unit; and a processing unit to obtain a spectral characteristic of background light emitted from the ambience of the measurement object, from the measurement light spectral characteristic and the spectral characteristic information on the possible background light.

14 Claims, 16 Drawing Sheets

(56) References Cited

U.S. PATENT DOCUMENTS

| | | | |
|---|---|---|---|
| 2017/0045437 A1 | 2/2017 | Ishimaru | |
| 2021/0310860 A1 | 10/2021 | Takashima | |

FOREIGN PATENT DOCUMENTS

| | | |
|---|---|---|
| JP | 2015-230229 A | 12/2015 |
| JP | 2020-24103 A | 2/2020 |
| WO | 2015/125918 A1 | 8/2015 |
| WO | 2020/175694 A1 | 9/2020 |

OTHER PUBLICATIONS

May 17, 2022 International Search Report issued in International Patent Application No. PCT/JP2022/016340.
May 17, 2022 Written Opinion issued in International Patent Application No. PCT/JP2022/016340.
Feb. 2, 2023 International Preliminary Report on Patentability issued in International Patent Application No. PCT/JP2022/016340.

\* cited by examiner

SPECTRAL MEASUREMENT DEVICE AND SPECTRAL MEASUREMENT METHOD

TECHNICAL FIELD

The present invention relates to a spectral measurement device and a spectral measurement method suitable for outdoor measurement of spectral characteristics.

BACKGROUND ART

Spectral measurement is one of techniques for qualitatively and quantitatively analyzing a measurement object (Patent Literature 1). A device used for spectral measurement (spectral measurement device) includes: a spectral optical system configured to disperse light emitted from a measurement object; a detector configured to detect the intensity of each light dispersed by the spectral optical system; and a processing unit configured to formulate a spectral characteristic (spectrum) of the measurement light from a detection result of the detector. Thus, the spectral measurement device specifies a component contained in the measurement object from the wavelength of a peak appearing in the spectrum or determines the amount of the component from the peak area. Herein, the light emitted from the measurement object includes: light emitted from the light source and reflected on the measurement object, transmitted light, fluorescent light emitted from the measurement object, light emitted from the measurement object itself (spontaneous light such as radiation light), and the like.

For example, when spectroscopically measuring a gas as a measurement object using the spectral measurement device, a container (sample container) in which the gas is contained and another container (control container) in which the inside is in a vacuum state are each irradiated with light from a light source, and spectral intensity of light transmitted through each container is detected by a detection unit. Then, the spectral characteristic of the measurement object is obtained from the result obtained by subtracting the spectral intensity of the transmitted light of the control container from the spectral intensity of the transmitted light of the sample container. Thus, it is possible to remove the influence of the transmitted light caused by the material of the container and the transmitted light caused by the gas present on the optical path from the container to the detector.

CITATION LIST

Patent Literature

Patent Literature 1: WO 2015/125918 A

SUMMARY OF INVENTION

Technical Problem

When a component of a gas is detected or an amount of the gas is measured outdoors, such as detecting a gas leak in a pipe of a gas installed in a factory site or identifying a component of a gas generated from soil, using the spectral measurement device, light existing around a measurement object can be substituted for light from a proper light source. For example, when a gas leak from a pipe is to be detected, reflection light of sunlight or illumination light reflected on the pipe, thermal radiation (radiation light) emitted from the pipe, or the like can be substituted for the light from a proper light source. In addition, for example, when a component of a gas emerging from the soil is specified, thermal radiation emitted from the soil can be substituted for the light from a proper light source. Of course, sunlight or illumination light itself can be used as the light from the light source. Such light is absorbed by the gas at the place where the gas is generated. Therefore, it is possible to detect occurrence of a gas leak, and to identify the components of the gas by measuring or monitoring the spectral characteristics of light at a place where gas generation is expected.

In the outdoors, various kinds of light (radiation light, reflected light, transmitted light, scattered light, and the like) are generated at various places, and these kinds of light (background light) are introduced into the spectral measurement device together with the light emitted from the measurement object. It is difficult to distinguish the background light from the light coming from the measurement object, and even if the direct sunlight is avoided, the background light often has a larger intensity than the light emitted from the measurement object. This brings about such a problem that a component of the measurement object cannot be identified and a type of the measurement object cannot be specified even if the spectral characteristic is measured in a state including the background light.

The case where the spectral measurement device is used outdoors has been described as an example, but even when the spectral measurement device is used indoors, a similar problem arises when it is difficult to distinguish between light emitted from the measurement object and background light for the measurement.

An object of the present invention is to provide a technique capable of accurately measuring a spectral characteristic of a measurement object even if it is difficult to distinguish between light emitted from the measurement object and background light.

Solution to Problem

A first mode of the present invention made to solve the above problems is a spectral measurement device configured to detect measurement light including light emitted from a measurement object and to measure a spectral characteristic of the light emitted from the measurement object from a result of the detection, the spectral measurement device comprising:

a spectral optical system configured to disperse the measurement light;

a detection unit configured to detect intensity of the measurement light dispersed by the spectral optical system;

a spectral characteristic acquisition unit configured to acquire a measurement light spectral characteristic indicating a relationship between a light intensity and a wavelength of the measurement light on a basis of a detection result of the detection unit;

a storage unit configured to store spectral characteristic information on possible background light, the information indicating the spectral characteristic of the possible background light, which involves a spectral sensitivity characteristic of an optical path of measurement light from the spectral optical system to the detection unit; and a processing unit configured to obtain a spectral characteristic of background light which is light emitted from an ambience of the measurement object, from the measurement light spectral characteristic and the spectral characteristic information on the possible background light.

A second mode of the present invention made to solve the above problems is a spectral measurement method for detecting measurement light including light emitted from a measurement object by a detection unit and measuring a spectral characteristic of the light emitted from the measurement object from the detection result, the spectral measurement method comprising:

a step of dispersing the measurement light by a spectral optical system;

a step of acquiring a spectral characteristic of the measurement light dispersed by the spectral optical system; and a step of obtaining a spectral characteristic of background light which is light emitted from an ambience of the measurement object, from a measurement light spectral characteristic and spectral characteristic information on possible background light, the information indicating the spectral characteristic of the possible background light, which involves spectral sensitivity characteristic of an optical path of the measurement light from the spectral optical system to the detection unit.

In the present invention, the light emitted from the measurement object includes light emitted from the measurement object itself (spontaneous light such as radiation light), and reflected light, transmitted light, fluorescent light, and the like generated when the measurement object is irradiated with light from the sunlight or light emitted from an artificial light source such as a lighting device (illumination light).

In addition, not only the measurement object but also an object existing around the measurement object is irradiated with sunlight or illumination light, and reflected light, transmitted light, fluorescent light, and the like are generated there. Reflected light, transmitted light, fluorescent light, and the like generated by irradiating the measurement object with light such as reflected light, transmitted light, fluorescent light, and radiation light generated in the object present around the measurement object can also be included in the light emitted from the measurement object. The spectral characteristic of the light emitted from the measurement object involves the property of the measurement object, so that by measuring the spectral characteristic of the light, qualitative analysis and quantitative analysis of the measurement object are possible.

It should be noted, both the light generated in the measurement object and the light generated around the measurement object are incident on the spectral measurement device as the measurement light. Therefore, the spectral characteristic obtained for the measurement light involves both the spectral characteristic of the light generated in the measurement object and the spectral characteristic of the light generated around the measurement object. In the present invention, light generated around the measurement object is referred to as "background light".

The measurement light incident on the spectral measurement device is dispersed by the spectral optical system and then incident on the detection unit, and the intensity of the dispersed light is detected by the detection unit. The measured intensity value by the detection unit depends on the spectral sensitivity characteristic of the optical element on the optical path from the spectral optical system to the detection unit, and thus the spectral characteristic of the background light involves the spectral sensitivity characteristic.

In the present invention, possible background light included in the measurement light is predicted, the spectral sensitivity characteristic is involved in the spectral characteristic of the possible background light, and this spectral characteristic information on the possible background light is stored in the storage unit. Then, the spectral characteristic of the background light of the measurement object is estimated from the spectral characteristic information on the possible background light and the spectral characteristic of the measurement light. Obtaining the spectral characteristic of the background light and thus a difference between the spectral characteristic and the spectral characteristic of the measurement light can determine the spectral characteristic of the light emitted from the measurement object. In addition, on a basis of the Lambert-Beer law, the absorbance of the measurement object can be calculated from the spectral characteristic of the light emitted from the measurement object and the spectral characteristic of the background light.

Herein, the spectral sensitivity characteristic of the optical path of the measurement light from the spectral optical system to the detection unit refers to, for example, a sum of the spectral sensitivity characteristics of all the optical elements and the spectral sensitivity characteristic of the detection unit when one or a plurality of optical elements such as an objective lens, a condenser lens, an imaging lens, and a mirror are present on the optical path. In a detector used in a spectral measurement device, typically, a relationship (photoelectric sensitivity) between a light intensity (incident light intensity) for each wavelength of light incident on (a light receiving element of) the detector and a photocurrent is determined previously, and the photoelectric sensitivity for each wavelength is referred to as spectral sensitivity characteristic. The photoelectric sensitivity is represented by quantum efficiency (%), a ratio between the incident light intensity (watt (W)) and photocurrent (ampere (A)), or relative sensitivity (%) when the photoelectric sensitivity at the maximum sensitivity wavelength is set to 100.

The possible background light can be determined according to conditions such as a place (outdoor or indoor) where the spectral characteristic of the measurement object is measured, a type of a light source that irradiates the measurement object with light, and a surrounding environment of the measurement object. For example, when the measurement place is outdoors, sunlight can be set as the possible background light. In addition, when the measurement place is indoor, light emitted from a light source can be set as the possible background light. Furthermore, black-body radiation at a plurality of temperatures may be set as the possible background light.

A black body is a theoretical substance (ideal black body) defined as an object that completely absorbs electromagnetic radiation incident from the outside over all wavelengths. The relationship between the spectral radiance of the black body and the wavelength for each temperature, that is, the spectral characteristic is represented by the following formula (1) as a function of the temperature and the wavelength according to the Planck's law of black body radiation.

[Formula 1]

$$I(\lambda, T) = \frac{2hc^2}{\lambda^5} \frac{1}{e^{hc/\lambda kT} - 1} \qquad (1)$$

In the formula (1), T represents a temperature [K], $\lambda$ represents a wavelength [nm], h represents a Planck constant, k represents a Boltzmann constant, and c represents a light velocity [m/s]. When the spectral characteristic of the black body radiation is used, by using the above formula (1) it is possible to easily calculate the information (spectral characteristic information on the possible background light) indicating the spectral characteristic of the possible background light, which involves the spectral sensitivity characteristic of the detection unit.

In addition, the spectral measurement device of the present invention or the spectral measurement method of the present invention is used to previously measure the spectral characteristic of light generated in a predetermined range around the measurement object, and the spectral characteristic can be stored as one of the spectral characteristic information on the possible background light.

As described above, the spectral characteristic obtained from the spectral measurement device or the spectral measurement method of the present invention involves the above-described spectral sensitivity characteristic for not only the spectral characteristic of the measurement object detected by the detection unit through the spectral optical system, but also the spectral characteristic of the background light.

The spectral characteristic information on the possible background light preferably includes spectral characteristics of a plurality of types of possible background light. Herein, the "plurality of types of possible background light" may include light emitted from a plurality of light sources of different types, a plurality of types of light emitted from one light source and having different intensities, light (black body radiation) emitted from a black body at different temperatures, and the like.

The processing unit obtains the spectral characteristic of the background light from the measurement light spectral characteristic and the information on the spectral characteristic of the possible background light. For example, when the intensity of the background light is significantly larger than the intensity of the light emitted from the measurement object, most of the measurement light is dominated by the background light, so that the spectral characteristic of the measurement light approximates to the spectral characteristic of the background light. Examples thereof include a case of measuring the spectral characteristic of light emitted from a pipe in order to detect gas leak of the pipe of gas outdoors, and a case of measuring the spectral characteristic of light emitted from a blood vessel such as a wrist and a back of a hand in order to measure a blood glucose level. In such a case, the processing unit extracts, as the background light spectral characteristic, a spectral characteristic approximate to the measurement light spectral characteristic from among the spectral characteristics of a plurality of types of the possible background light. Examples of the method of extracting the spectral characteristic approximate to the measurement light spectral characteristic from the spectral characteristics of a plurality of types of the possible background light include a process (fitting process) of sequentially fitting the spectral characteristic of a plurality of types of the possible background light to the measurement light spectral characteristic and extracting the most fitted spectral characteristic as the background light spectral characteristic.

Advantageous Effects of Invention

The present invention can accurately measure the spectral characteristic of the measurement object when it is difficult to distinguish between the light emitted from the measurement object and the background light as in the case of measuring the spectral characteristic of the blood flowing in the blood vessel through the skin or in the case of measuring the spectral characteristic of the measurement object outdoors.

BRIEF DESCRIPTION OF DRAWINGS

FIG. 4A is a graph illustrating a relationship between the spectral radiance of the black body and a wavelength, FIG. 4B is a graph illustrating a relationship between light receiving sensitivity of a detector and a wavelength, and FIG. 4C is a graph illustrating a relationship between the radiance and the wavelength after correction with the light receiving sensitivity of the detector.

(FIG. 11A), spectral radiance of the black body (FIG. 11B), and a spectral sensitivity characteristic of a spectral measurement device 100, in Second Example with measuring a spectral characteristic of the measurement object (dye powder) using the spectral measurement device of the present embodiment.

DESCRIPTION OF EMBODIMENTS

Hereinafter, embodiments of the present invention will be described with reference to the drawings.
[Configuration of Spectral Measurement Device]

Figure 1A:
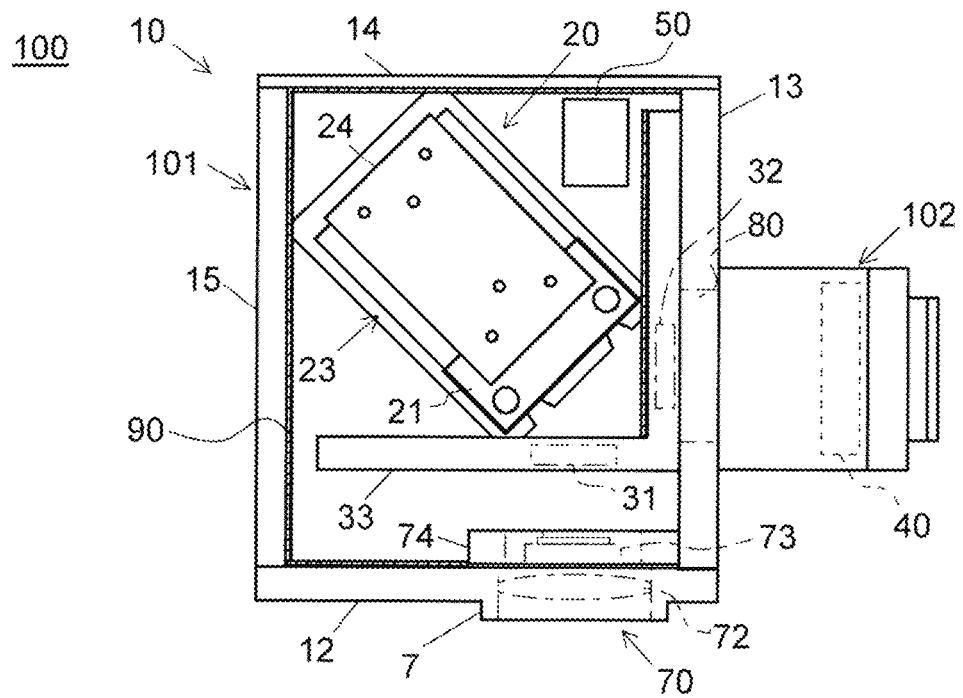
FIG. 1A is a top view illustrating a spectral measurement device with a part of a housing omitted.
Figure 1B:
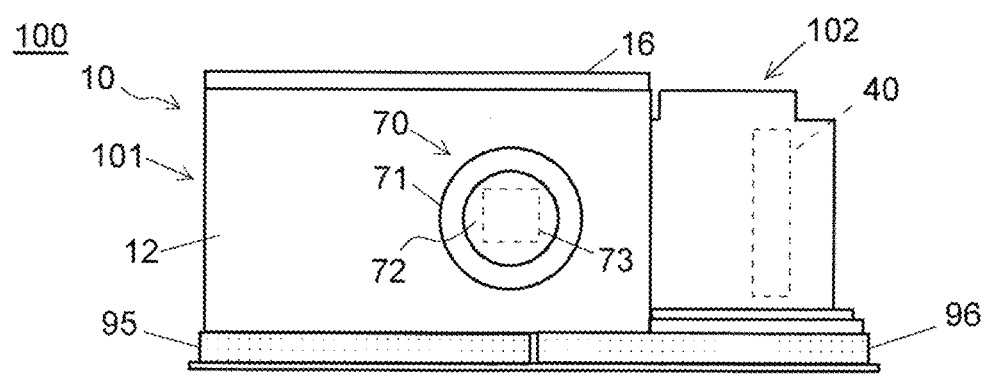
FIG. 1B is a side view of the spectral measurement device.
Figure 1C:
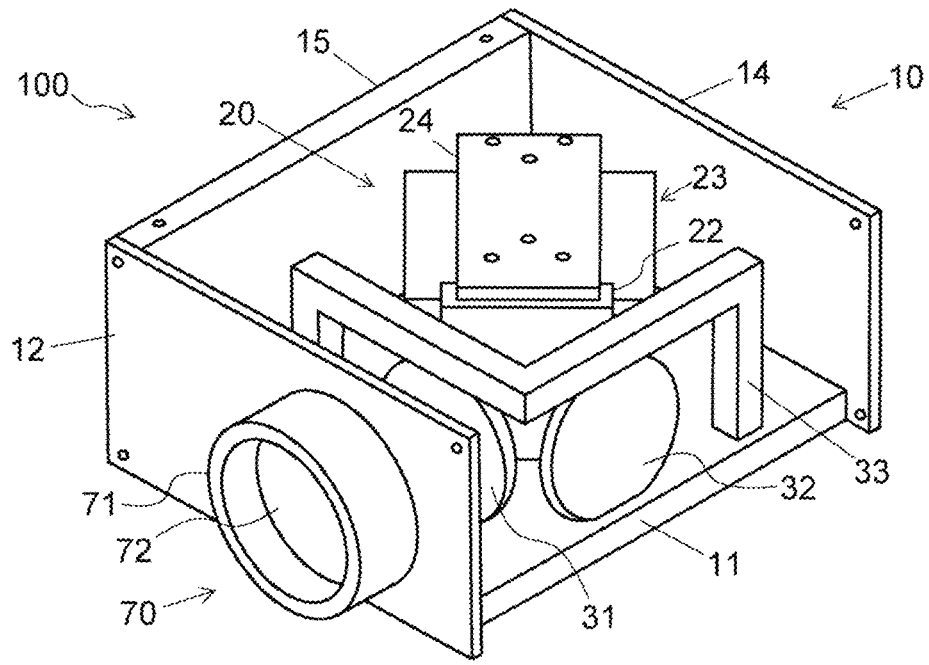
FIG. 1C is a perspective view illustrating the spectral measurement device with a part of a housing omitted.
Figure 2A:
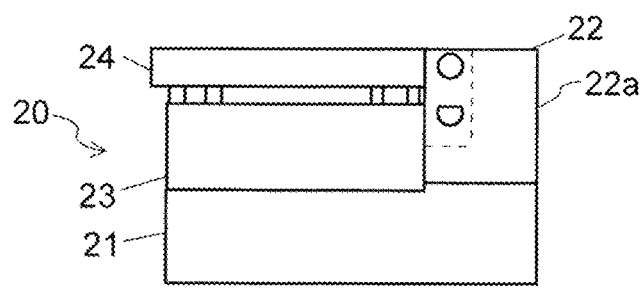
FIG. 2A is a side view of a phase shifter.
Figure 2B:
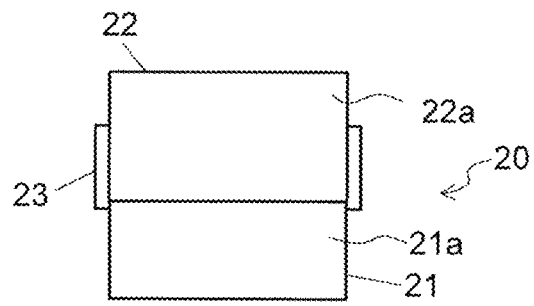
FIG. 2B is a view of the phase shifter as viewed from a reflection face side.

A configuration of the spectral measurement device according to an embodiment of the present invention will be described with reference to FIGS. 1A to 1C, 2A, and 2B. In FIGS. 1A and 1C, a part of the housing is omitted so that the internal structure of the spectral measurement device can be seen.

A spectral measurement device 100 is made of a housing 10, and a phase shifter 20, an objective lens 31, an imaging lens 32, and a detector 40 housed in the housing. The housing 10 includes two large and small rectangular box-shaped housings 101 and 102. Hereinafter, the larger one is referred to as first housing 101, and the smaller one is referred to as second housing 102. The phase shifter 20 corresponds to a spectral optical system of the present invention. The phase shifter 20, the objective lens 31, and the imaging lens 32 are housed in the first housing 101, and the detector 40 is housed in the second housing 102.

The first housing 101 is made of a rectangular plate-shaped base plate 11, four pieces of side wall portions 12 to 15, and a lid 16. The side wall portions 12 to 15 are detachably connected to each other, the side wall portions 12 to 15 and the base plate 11, and the side wall portions 12 to 15 and the lid 16 are detachably connected to each other by screws (not illustrated).

The objective lens 31 is disposed on the base plate 11 such that its lens face is parallel to the side wall portion 12. The imaging lens 32 is disposed on the base plate 11 such that its lens face is parallel to the side wall portion 13. The objective lens 31 and the imaging lens 32 are held between a lens holder 33 erected on the upper face of the base plate 11 and the base plate 11. The lens holder 33 is made of an L-shaped member in top view and a pair of legs, and lower ends of the pair of legs are fixed to the upper face of the base plate 11. Recesses are formed in appropriate portions of the upper face of the base plate 11 corresponding to the arrangement of the phase shifter 20, the objective lens 31, the imaging lens 32, and the lens holder 33. The lower end portion of the objective lens 31, the lower end portion of the imaging lens 32, and the lower end portion of the leg portion of the lens holder 33 are inserted into these recesses to position the objective lens 31 and the imaging lens 32.

An introduction port 70 for introducing measurement light into the housing 10 is provided at a portion of the side wall portion 12 facing the objective lens 31. The introduction port 70 is made of a cylindrical portion 71 protruding outward from the side wall portion 12, a condenser lens 72 fitted into the cylindrical portion 71, and a conjugate plane lattice 73 disposed between the condenser lens 72 and the objective lens 31 and on a conjugate plane of the objective lens 31. A conjugate plane lattice 73 is held by a grid holder 74 erected on the upper face of the base plate 11.

A lead-out port 80 for measurement light (reflected light) having passed through the imaging lens 32 is provided in a portion of the side wall portion 13 facing the imaging lens 32, and the second housing 102 is attached to an outer face of the side wall portion 13 in a portion where the lead-out port 80 is formed. In the second housing 102, the detector is disposed such that the light receiving face faces the lead-out port 80 and the light receiving face is located on the imaging face of the imaging lens 32. The detector 40 is made of a two-dimensional array sensor having a plurality of light receiving elements two-dimensionally disposed on a light receiving face.

The phase shifter 20 is made of a fixed reflection member 21, a movable reflection member 22, and a drive mechanism 23 which drives the movable reflection member 22. The fixed reflection member 21 is made of a cuboidal metal block, and its one face is mirror-finished to form a reflection face 21a (hereinafter, also referred to as fixed reflection face 21a). The fixed reflection member 21 is fixed to the upper face of the base plate 11 such that the reflection face 21a is inclined by 45° with respect to each optical axis of the objective lens 31 and the imaging lens 32.

A drive mechanism 23 is fixed to an upper face of the fixed reflection member 21. The drive mechanism 23 is made of, for example, an ultrasonic motor, and moves the moving body 24 disposed above the drive mechanism 23 in the horizontal direction. The moving body 24 is made of a member having an L-shaped cross section and having an attachment plate portion 24a and an attachment end portion 24b bent downward from the end portion, and is attached to an upper portion of the drive mechanism 23 by the attachment plate portion 24a. The drive mechanism 23 is fixed to the upper face of the fixed reflection member 21 such that the moving direction of the moving body 24 coincides with the normal direction of the fixed reflection face 21a.

The movable reflection member 22 is fixed to the attachment end portion 24b of the moving body 24. The movable reflection member 22 is made of a cuboidal metal block, and has a reflection face 22a (hereinafter, also referred to as movable reflection face 22a) obtained by mirror-finishing its one face, and a fitting recess 22b formed on a face (back face) opposite to the reflection face 22a and fitted to the attachment end portion 24b. The reflection face 22a of the movable reflection member 22 has substantially the same size as the reflection face 21a of the fixed reflection member 21.

Figure 3:
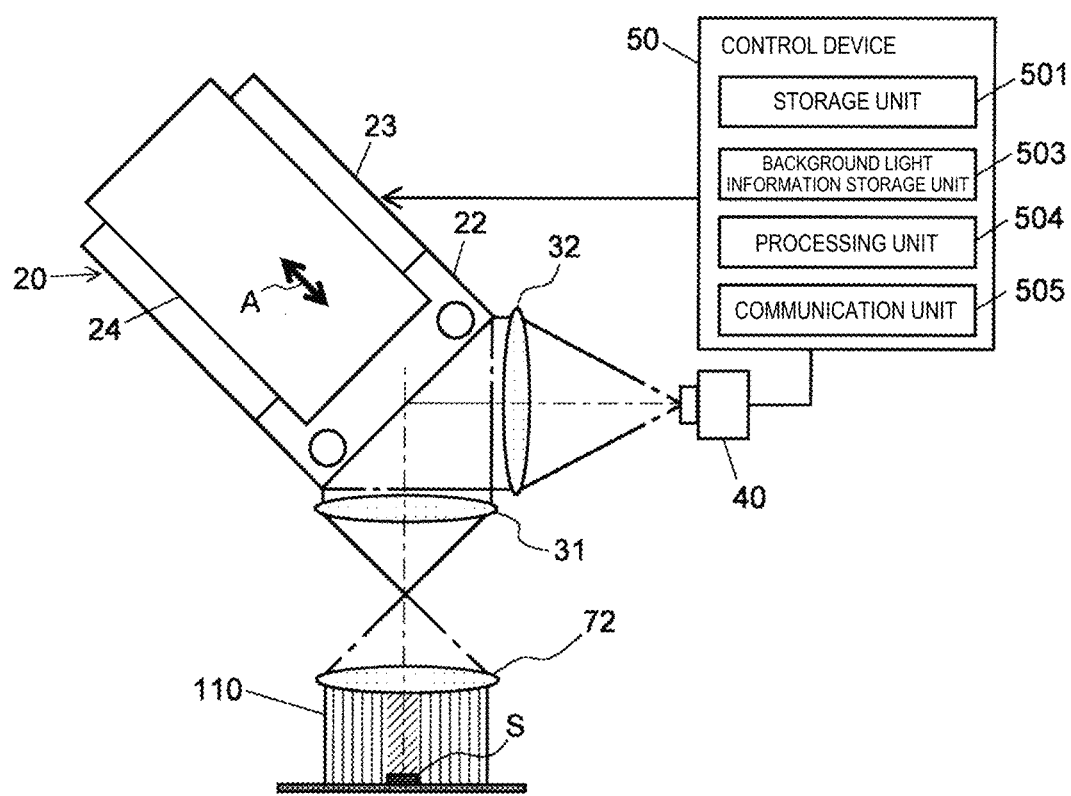
FIG. 3 is an operation explanatory view of the spectral measurement device.

A control device 50 configured to control the operation of the spectral measurement device 100 is accommodated in the first housing 101. As illustrated in FIG. 3, the drive mechanism 23 and the detector 40 are connected to the control device 50. In addition, the control device 50 has a storage unit 501, a background light information storage unit 503, a processing unit 504, and a communication unit 505. The storage unit 501 stores a control program for controlling operations of the drive mechanism 23, the detector 40, and the like.

The background light information storage unit 503 corresponds to a storage unit of the present invention. The background light information storage unit 503 stores information on the spectral characteristic of possible background light (hereinafter referred to as "background light information"). The "background light" refers to light excluding light emitted from the measurement object among the measurement lights introduced into the spectral measurement device 100. The background light information corresponds to the spectral characteristic information on the possible background light for the present invention. In the present embodiment, the background light information is calculated from the spectral radiance of the black body, which is an ideal radiator, and the spectral sensitivity characteristic of the spectral measurement device 100. The spectral radiance I of the black body is represented by the following formula (1) as a function of temperature and wavelength according to Planck's law of black body radiation (Planck's law).

[Formula 1]

$$I(\lambda, T) = \frac{2hc^2}{\lambda^5} \frac{1}{e^{hc/\lambda kT} - 1} \quad (1)$$

In addition, the spectral sensitivity characteristic of the spectral measurement device 100 is a concept of integrating the spectral sensitivity characteristic of the optical path of the measurement light from the introduction port 70 of the spectral measurement device 100 to the detector 40, specifically, the spectral sensitivity characteristic of a plurality of optical elements located on the optical path, and the spectral sensitivity characteristic of the detector 40. The optical element includes a condenser lens 72, an objective lens 31, a fixed reflection member 21, a movable reflection member 22, and an imaging lens 32. The spectral sensitivity characteristic of the detector 40 refers to a relationship (photoelectric sensitivity) between a light intensity (incident light intensity) and a photocurrent for each wavelength of light incident on the detector 40, and is determined by the detector 40. The photoelectric sensitivity is represented by quantum efficiency (%), a ratio between the incident light intensity (watt (W)) and photocurrent (ampere (A)), or relative sensitivity (%) when the photoelectric sensitivity at the maximum sensitivity wavelength is set to 100. In the present embodiment, a value obtained by multiplying the spectral radiance of the black body in the measurement wavelength range of the detector 40 by the spectral sensitivity coefficient (relative sensitivity coefficient) of the spectral measurement device 100 is stored in the background light information storage unit 503 as the background light information.

Figure 4A:
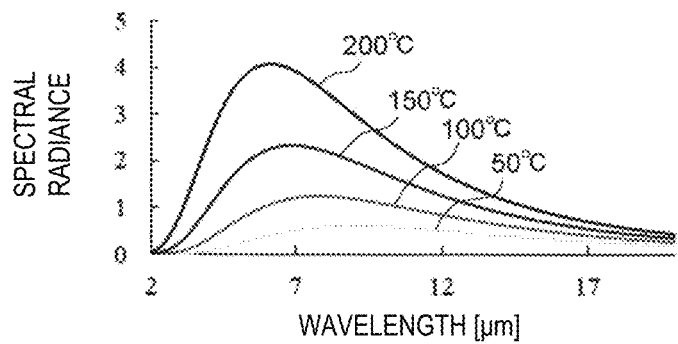
FIGS. 4A, 4B, and 4C are views for explaining a method for obtaining a spectral characteristic of background light on a basis of spectral radiance of a black body.
Figure 4B:
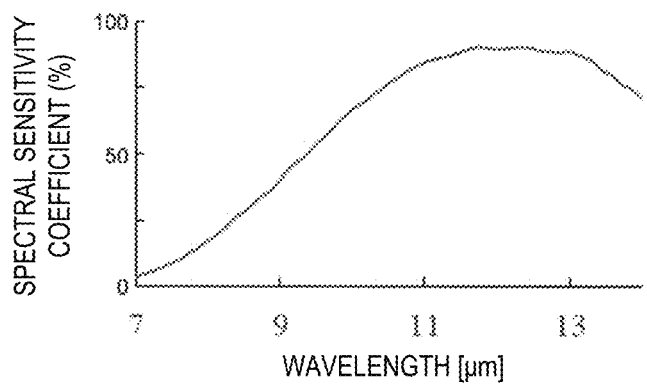
Figure 4C:
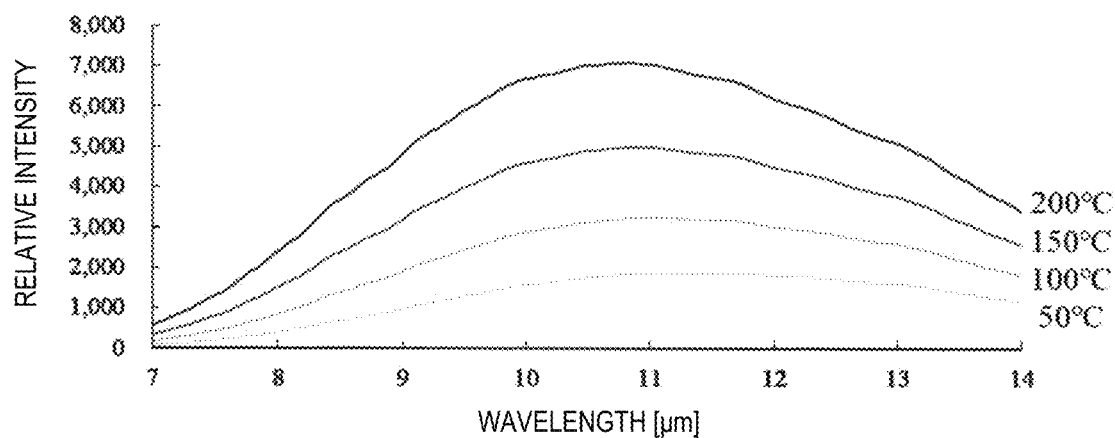

For example, the graph of FIG. 4A illustrates the relationship between the spectral radiance of the black body and the wavelength at temperatures of 50° C., 100° C., 150° C., and 200° C., and the graph of FIG. 4B illustrates the relationship between the spectral sensitivity coefficient (%) of the spectral measurement device 100 and the wavelength. In FIG. 4A, the horizontal axis represents the wavelength, and the vertical axis represents the spectral radiance. In FIG. 4B, the horizontal axis represents the wavelength, and the vertical axis represents the spectral sensitivity coefficient. In such an example, the information stored in the background light information storage unit 503 is set to a graph representing a spectral radiance spectrum of the black body as illustrated in FIG. 4C or coordinate value data of each point on the graph.

The processing unit 504 obtains an interferogram from the detection signal of the detector 40 input to the control device 50, and mathematically performs Fourier transform on the interferogram to obtain a spectral characteristic which is a relative intensity for each wavelength of the measurement light. In addition, the processing unit 504 estimates the spectral characteristic of the background light included in the measurement light from the spectral characteristic of the measurement light and the background light information stored in the background light information storage unit 503. Then, the spectral characteristic of the measurement object is determined from the difference between the spectral characteristic of the estimated background light and the spectral characteristic of the measurement light. Therefore, the processing unit 504 stores a data processing program for obtaining the spectral characteristic of the measurement object. In the present embodiment, the detector 40 and the processing unit 504 constitute the detection unit of the present invention. In addition, the processing unit 504 functions as a spectral characteristic acquisition unit and a processing unit of the present invention.

The communication unit 505 is for connecting the control device 50 to an external device such as a personal computer or a printer via a communication line such as the Internet. With such a configuration, data such as spectral characteristic of the measurement object obtained by the processing unit 504 can be output to a display, a printer, or the like of a personal computer through the communication unit 505. Furthermore, herein, it is described that the control device 50 provided inside the first housing 101 has the functions of the background light information storage unit 503 and the processing unit 504, but the detection result of the detector 40 may be transferred to a personal computer via the communication unit 505 and the Internet and processed in the computer. In this case, the personal computer has the above-described data processing program installed and a memory with the background light information stored. In this configuration, the CPU of the personal computer functions as a processing unit, and the memory functions as a background light information storage unit.

[Measurement of Spectral Characteristic of Measurement Light]

The measurement operation of the spectral characteristic of the measurement light using the spectral measurement device 100 having the above configuration will be described with reference to FIG. 3. A method of measuring spectral characteristics using the spectral measurement device 100 is called imaging type two-dimensional Fourier spectroscopy.

First, the drive mechanism 23 of the phase shifter 20 of the spectral measurement device 100 is operated to reciprocate the movable reflection member 22 in a direction indicated by an arrow A in FIG. 3. More specifically, the movable reflection member 22 is reciprocated at a constant speed between a reference position where the movable reflection face 22a and the fixed reflection face 21a are on the same plane and a variation position where the movable reflection face 22a is behind the fixed reflection face 21a. The drive of the drive mechanism 23 is controlled by the control device 50.

Subsequently, the spectral measurement device 100 is provided such that the introduction port 70 of the spectral measurement device 100 faces a measurement object S. As a result, a measurement light 110 including the light emitted from the measurement object S enters the first housing 101 from the introduction port 70. The measurement light 110 incident on the first housing 101 passes through the condenser lens 72 and the objective lens 31, becomes parallel light, and reaches the phase shifter 20. The measurement light 110 reaching the phase shifter 20 is incident on both the fixed reflection face 21a and the movable reflection face 22a so as to straddle both the reflection faces, and is reflected by each of the reflection faces.

The light reflected by the fixed reflection face 21a (fixed reflection light) and the light reflected by the movable reflection face 22a (movable reflection light) pass through the imaging lens 32 and then enter the second housing 102 from the lead-out port 80, and are condensed on the light receiving face of the detector 40 to form interference light. A plurality of light receiving elements is disposed on the light receiving face of the detector 40, and the detector 40 generates a detection signal corresponding to the intensity of the interference light incident on each light receiving element and outputs the detection signal to the control device 50.

The detection signal input from the detector 40 to the control device 50 is processed by the processing unit 504 to acquire an interferogram indicating the intensity change of the interference light, and this interferogram is mathematically Fourier-transformed to acquire the spectral characteristic (spectrum) of the measurement light 110. In the spectral measurement device 100 according to the present embodiment, a plurality of light receiving elements are two-dimensionally disposed on the light receiving face of the detector 40, and thus the spectral characteristic of the measurement light 110 can be two-dimensionally measured.

[Calculation of Spectral Characteristic of Measurement Object]

When the spectral characteristic of the measurement light 110 is calculated, the processing unit 504 estimates the spectral characteristic of the background light included in the measurement light 110 from the spectral characteristic of the measurement light 110 and the background light information stored in the background light information storage unit 503. Examples of the estimation method include a method in which the spectral characteristic having the smallest difference from the spectral characteristic of the measurement light is used as the spectral characteristic of the background light from among the spectral radiance spectra of the black body related to a plurality of temperatures stored in the background light information storage unit 503 using the least squares method. The spectral characteristic of the background light is determined by fitting a graph representing the spectral radiance spectrum of the black body at each temperature in an envelope shape on the upper side of the graph representing the spectrum of the measurement light (that is, so as to be in contact with the graph peak) or in an envelope shape on the lower side of the graph (that is, so as to be in contact with the graph bottom). For the fitting processing, a nonlinear least squares method such as a Newton method, a pattern method, or a Gauss-Newton method can be used.

When the background light included in the measurement light is estimated in order to measure the spectral characteristic of the light generated in the measurement object S (this is referred to as active spectral characteristic) by irradiating the measurement object S with the light from the light source, the graph representing the spectral radiance spectrum of the black body is preferably fitted in an envelope shape on the upper side of the graph representing the spectrum of the measurement light. When the background light included in the measurement light is estimated in order to measure the spectral characteristic of the light emitted from the measurement object S itself (this is referred to as passive spectral characteristic), the graph representing the spectral radiance spectrum of the black body is preferably fitted in an envelope shape on the lower side of the graph representing the spectrum of the measurement light. When the spectral characteristic of the light generated in the measurement object S is qualitatively evaluated, the spectral characteristic of the background light is preferably estimated from the spectral radiance spectrum of the black body using the least squares method.

Figure 5:
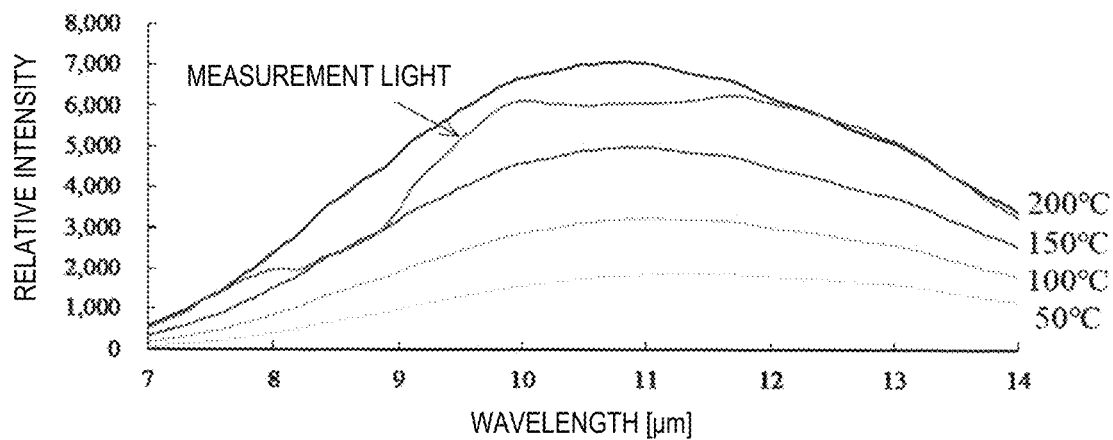
FIG. 5 is a graph illustrating a relationship between spectral radiance of the black body and a wavelength after a spectral characteristic (spectrum) of measurement light is corrected by light receiving sensitivity of the detector.

For example, FIG. 5 illustrates a result of searching, among spectral radiance spectrums at temperatures illustrated in FIG. 4C, a spectral radiance spectrum fitted in an envelope shape on the upper side of the graph (spectrum) representing the spectral characteristic of the measurement light 110. As illustrated in FIG. 5, the graph representing the spectral radiance spectrum at the temperature of 200° C. is fitted in an envelope shape on the upper side of the spectrum of the measurement light, and thus the processing unit 504 estimates the spectral radiance spectrum at the temperature of 200° C. as the background light spectrum (spectral characteristic of the background light).

Figure 6:
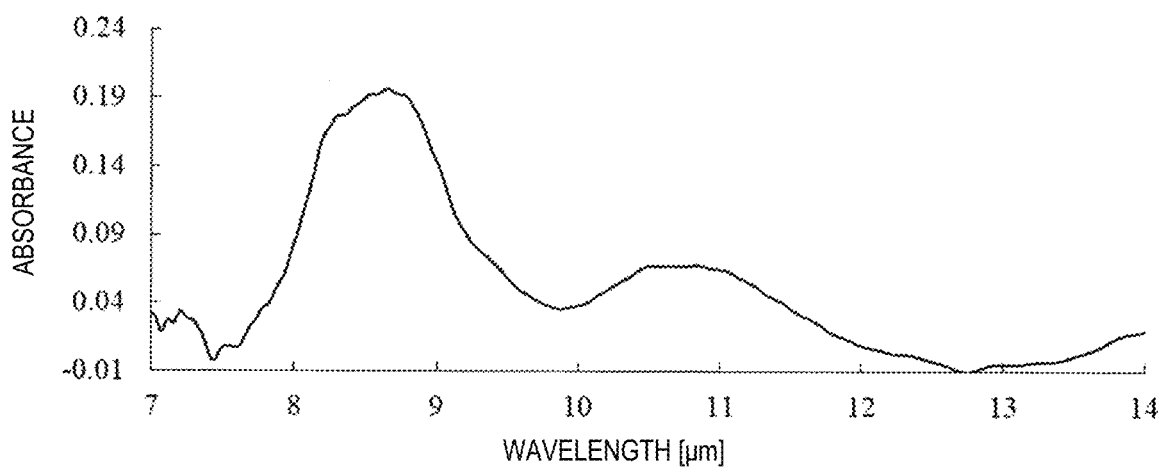
FIG. 6 illustrates a spectral characteristic (spectrum) of a measurement object.

Then, the processing unit 504 obtains a difference between the estimated spectral characteristic of the background light and the spectral characteristic of the measurement light 110, and sets this difference as the spectral characteristic of the light emitted from the measurement object. The absorbance of the measurement object is calculated from the spectral characteristic of the light emitted from the measurement object and the spectral characteristic of the background light using the following relational formula (2) based on the Lambert-Beer law. FIG. 6 illustrates the absorbance of the measurement object obtained when the spectral characteristic of the light emitted from the measurement object is as illustrated in FIG. 5. Herein, the intensity of the measurement light 110 is referred to as "incident light intensity" in the formula (2).

[Formula 2]

$$\text{Absorbance} = -\log_{10} \frac{\text{Transmitted light intensity}}{\text{Incident light intensity}} \qquad (2)$$

Then, an embodiment in which spectral characteristics of light emitted from a measurement object in some specific model environments are measured will be described.

First Example

Figure 7:
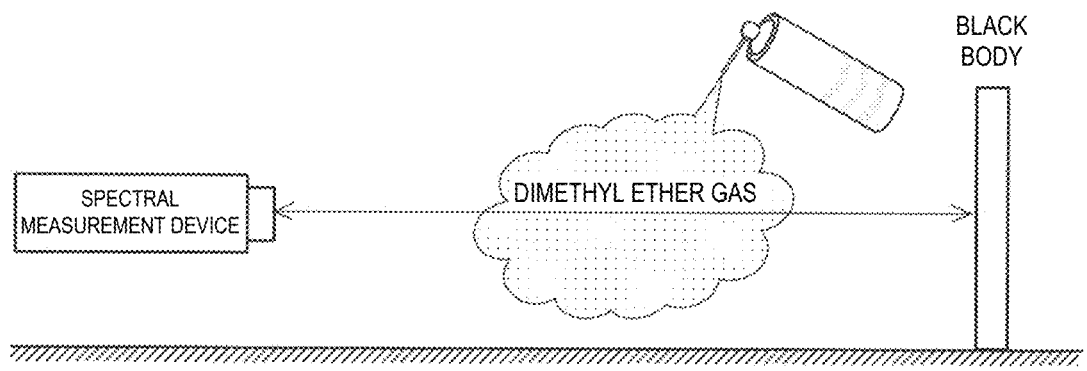
FIG. 7 is a view illustrating a model environment of First Example in which a spectral characteristic of the measurement object (dimethyl ether gas) was measured using the spectral measurement device of the present embodiment.

First Example is an example in which an active spectral characteristic of a measurement object is measured using a black body at a predetermined temperature as a light source. In this example, there was measured a spectral characteristic of light emitted from dimethyl ether gas as a measurement object in a model environment in which a black body set to a temperature of 200° C. was installed as illustrated in FIG. 7, that is, a spectral characteristic of the black body radiation light that has passed through the dimethyl ether gas. In the model environment illustrated in FIG. 7, a black body is installed at a position of 780 mm from the imaging lens of the spectral measurement device 100. In addition, there was used the detector 40 having a measurement visual field (150×150 pixels) corresponding to a radiation face of the black body.

Figure 8:
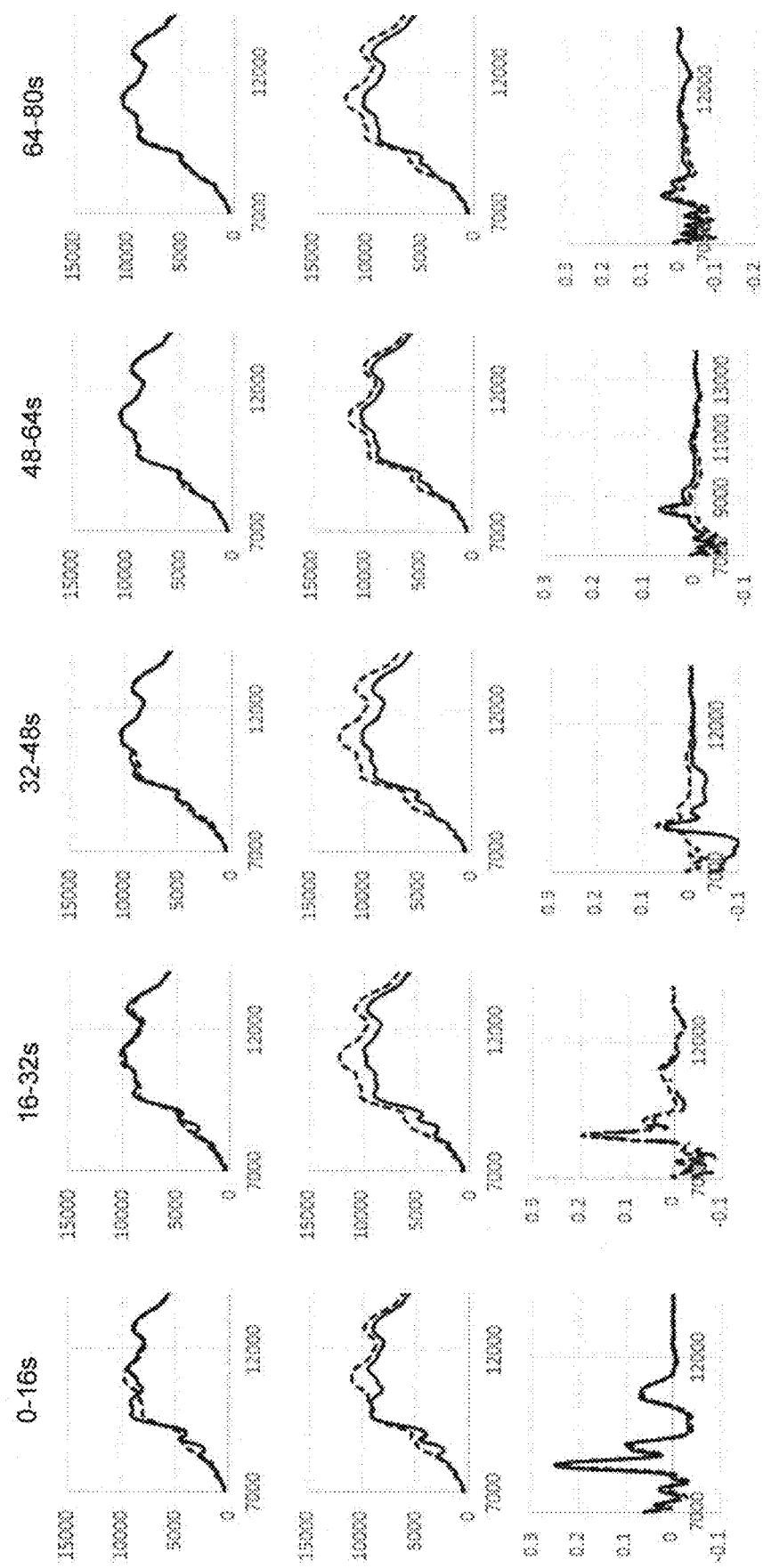
FIG. 8 includes: an upper view illustrating a background light spectrum and a measurement light spectrum estimated by a fitting process using a least squares method; a middle view illustrating a background light spectrum and a measurement light spectrum estimated by an envelope fitting process; and a lower view illustrating an absorption spectrum of the measurement object (dimethyl ether) obtained by the fitting process using the least squares method and the envelope fitting process.

First, dimethyl ether gas was injected from a spray can between the black body and the spectral measurement device 100 for 15 seconds, and then a spectral characteristic of the measurement light was measured every 16 seconds. Then, the spectral radiance spectrum of the black body at each temperature was fitted to the spectral spectrum of the measurement light in each time range to estimate the background light spectrum. The background light spectrum was estimated by a fitting process using a least squares method and a process of fitting a spectral spectrum of the measurement light in an envelope shape, and the background light spectrums obtained in each process were compared. In this example, in order to measure an absorption spectral characteristic (active spectral characteristic) of dimethyl ether gas from transmitted light of the dimethyl ether gas, a spectral radiance spectrum of the black body was fitted in an envelope shape on an upper side of the spectral spectrum of the measurement light. The upper part of FIG. 8 is a view illustrating the background light spectrum estimated by the fitting processing using the least squares method, and the middle part is a view illustrating the background light spectrum estimated by the envelope fitting processing together with the measurement light spectrum. In each view, the horizontal axis of the graph represents wavelength, and the vertical axis represents relative intensity. Furthermore, a solid line curve represents a measurement light spectrum, and a broken line curve represents a background light spectrum.

The lower part of FIG. 8 illustrates an absorption spectrum of the measurement object (dimethyl ether gas) calculated by determining respective differences between the measurement light spectrum and respective background light spectrums obtained by the above-described two types of fitting processing, and by using this difference and the above-described relational formula (2). The horizontal axis of each graph in the lower part of FIG. 8 represents wavelength, and the vertical axis represents absorbance. In addition, the solid curve represents an absorption spectrum obtained from a background light spectrum estimated by the envelope fitting process, and the broken curve represents an absorption spectrum obtained from a background light spectrum estimated by a fitting process using a least squares method. As illustrated in the lower part of FIG. 8, an absorption peak was observed in substantially the same wavelength range in any fitting process. That is, it has been found that substantially similar absorption spectrums can be obtained in using at least the above two types of fitting processes.

Figure 9:
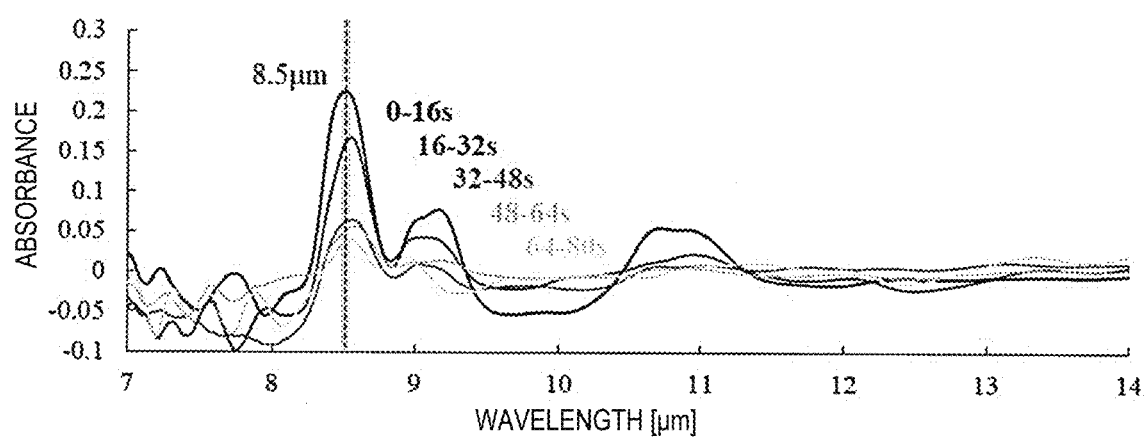
FIG. 9 is an absorption spectrum in each time range of dimethyl ether gas obtained by the envelope fitting process.

FIG. 9 is an absorption spectrum in each time range of dimethyl ether gas obtained by the envelope fitting process. It has been found from FIG. 9 that an absorption peak (wavelength λ=8.5 μm) unique to dimethyl ether was confirmed in the absorption spectrum in any time range, and the absorbance decreased with the lapse of time.

Figure 10:
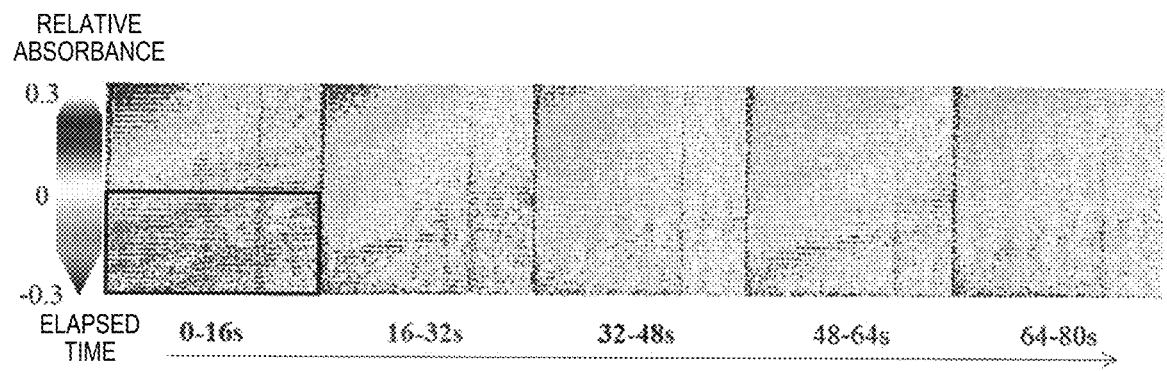
FIG. 10 is a pseudo color image of absorbance of dimethyl ether gas in a measurement visual field in each time range.

FIG. 10 illustrates a pseudo color image obtained by visualizing the absorbance in the measurement visual field based on the absorbance at 8.5 μm, which is the absorption wavelength of dimethyl ether. FIG. 10 is actually a color image, but is represented in black and white herein. In this pseudo color image, colors are painted in 10 stages according to the magnitude of the absorbance in the measurement visual field, and in the actual image, the maximum value of the absorbance is represented in red and the minimum value is represented in green. The absorbance increases as the gas concentration of dimethyl ether increases, and thus it has been confirmed from FIG. 10 that the gas concentration decreases with the lapse of time. In addition, the gas concentration was higher in the lower half of the measurement visual field as a whole. This result was consistent with the fact that dimethyl ether gas has a larger specific gravity than air.

Second Example

Second Example is an example of measuring a passive spectral characteristic of a measurement object. In this example, powder of a dye (alizarin, indigo) as a measurement object was placed on an aluminum plate heated to 125° C., the powder of the dye was heated, and spectral characteristics of light (radiation light) emitted from the powder of the dye were determined. The radiation factor of aluminum is about 0.05, and the intensity of the radiation light emitted from the plate by heating the plate is significantly small as compared with the intensity of the radiation light emitted from the dye powder, and can be thus ignored. Therefore, in the present example, the spectral radiance I (λ, T) of the black body represented by the above-described formula (1) is set as the spectral characteristic of the possible background light.

Figure 11A:
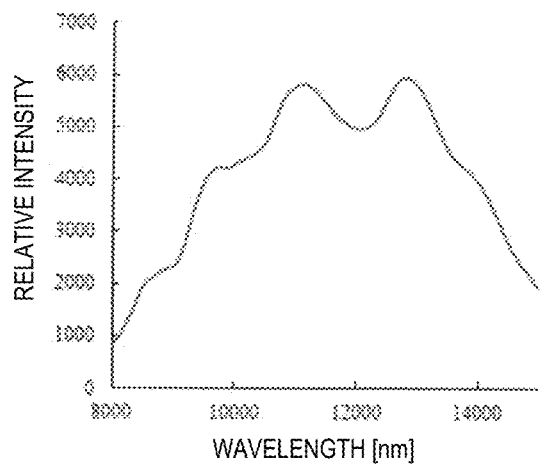
FIGS. 11A, 11B, and 11C are graphs illustrating relationships between a wavelength and an actually measured intensity of radiation light from a metal plate heated to 125° C.
Figure 11B:
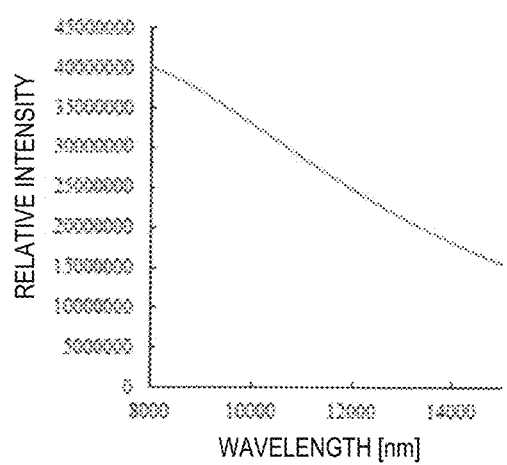

First, the spectral characteristic of the black body heated to 125° C. was measured using the spectral measurement device 100 to determine the spectral sensitivity coefficient of the spectral measurement device 100. FIG. 11A illustrates an actual measurement value of the spectral characteristic of the black body heated to 125° C., and FIG. 11B illustrates the spectral radiance I (λ, 125° C.) when 125° C. is substituted for temperature T in the formula (1). In FIGS. 11A and 11B, the horizontal axis of the graph represents wavelength (nm), and the vertical axis represents relative intensity.

When the measured value is I' (λ, 125° C.) and the spectral sensitivity coefficient of the spectral measurement device 100 is Sp, I' (λ, 125° C.) can be represented by the following formula (3) using I (λ, 125° C.) and Sp, so that the spectral sensitivity coefficient Sp can be obtained from I'(λ, 125° C.) and I (λ, 125° C.).

$$I'(\lambda, 125° C.) = I(\lambda, 125° C.) \times Sp \quad (3)$$

Figure 11C:
Figure 11C:
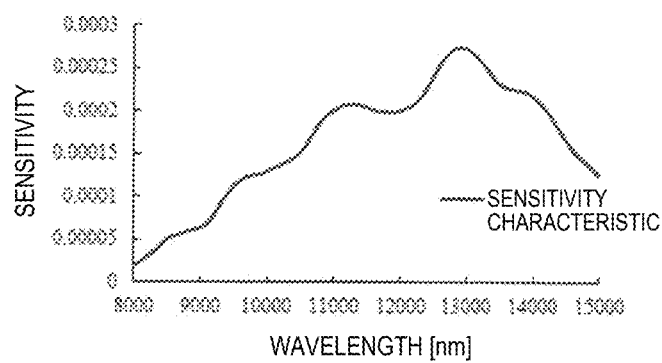

FIG. 11C is a graph illustrating the relationship between the spectral sensitivity coefficient obtained from I' (λ, 125° C.) and I (λ, 125° C.) and the wavelength. The horizontal axis of this graph represents wavelength, and the vertical axis represents sensitivity.

Then, the powder of alizarin and the powder of indigo were respectively placed on an aluminum plate heated to 125° C., and the spectral characteristics of the radiation light (that is, the measurement light) emitted from the powder heated to about 125° C. were measured using the spectral measurement device 100. The thermal radiation spectrum of the black body around 125° C. was multiplied by the spectral sensitivity coefficient Sp, this value was fitted to the graph (spectrum) of the spectral characteristic of the measurement light, and thus the background light spectrum was estimated. In this example, in order to measure the spectral characteristic (passive spectral characteristic) of the radiation light emitted from the measurement object itself, the value obtained by multiplying the thermal radiation spectrum of the black body by the sensitivity coefficient was fitted in an envelope shape on the lower side of the spectrum of the measurement light.

Figure 12A:
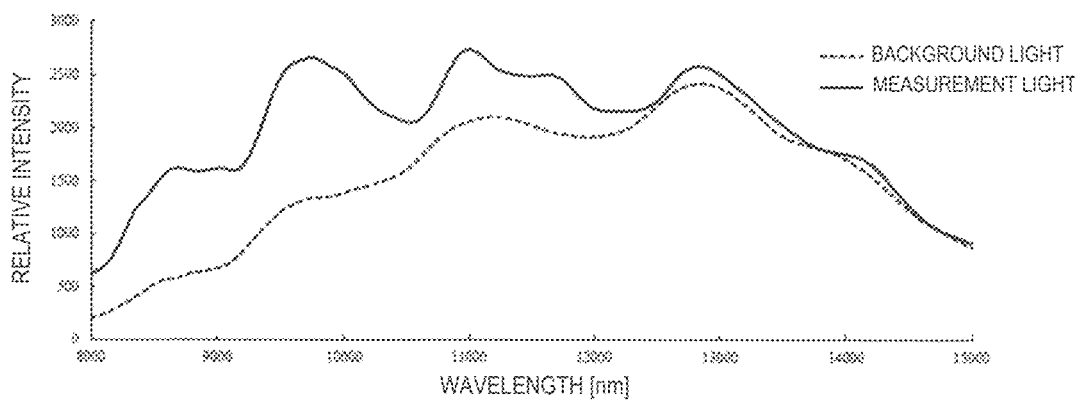
FIG. 12A illustrates spectrums of measurement light measured with alizarin powder placed on a metal plate and estimated background light.
Figure 12B:
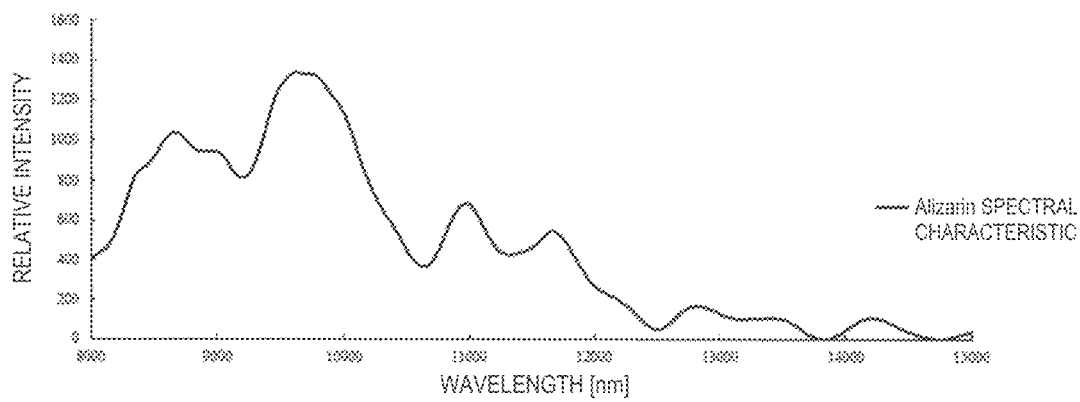
FIG. 12B illustrates a spectrum of radiation light of alizarin.
Figure 13:
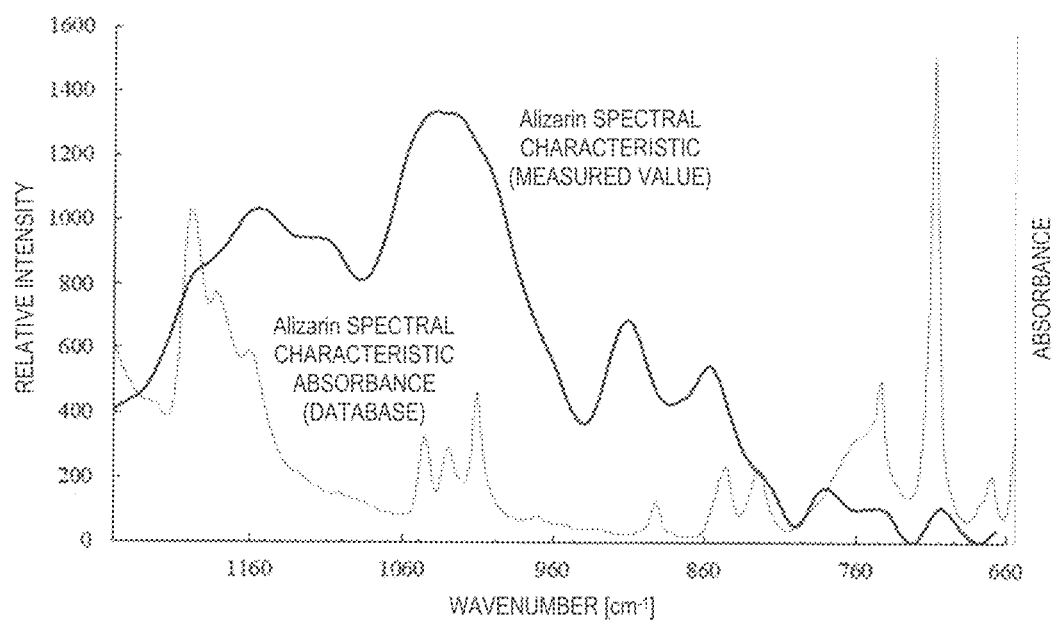
FIG. 13 is a view illustrating a spectrum of radiation light of alizarin and an alizarin spectral characteristic acquired from a known database.
Figure 14:
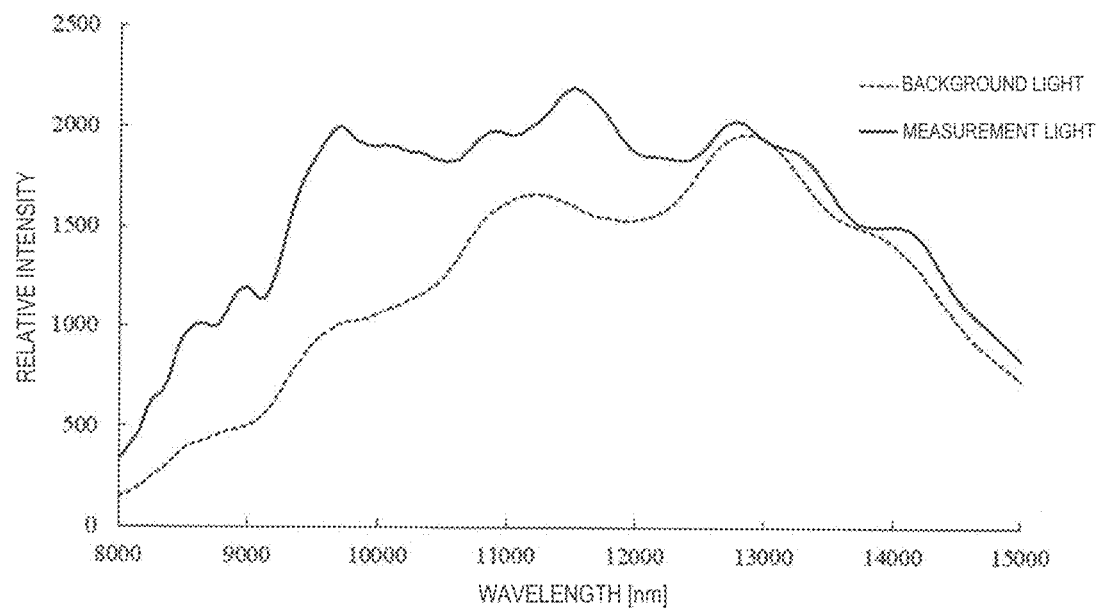
FIG. 14 is spectrums of measurement light measured with indigo powder placed on a metal plate and estimated background light.
Figure 15:
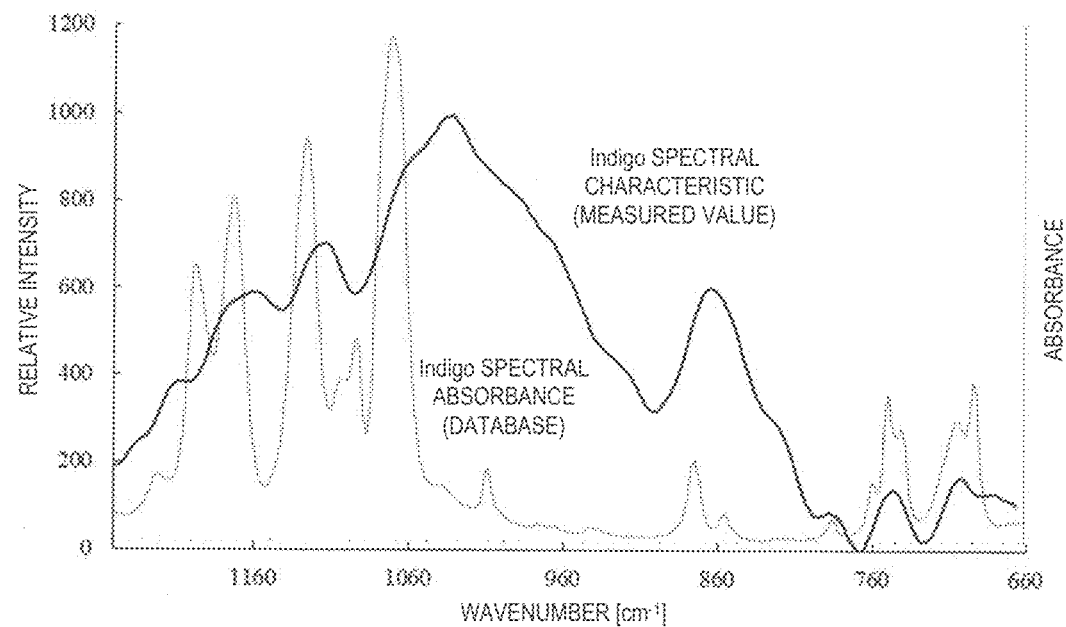
FIG. 15 is a view illustrating a spectrum of indigo radiation light and an indigo spectral characteristic acquired from a known database.

FIGS. 12A and 14 each illustrate the spectrum of the measurement light measured in a state where the powder of alizarin and the powder of indigo were placed on a metal plate, and the background light spectrum estimated by the above-described fitting process. FIG. 12B illustrates a radiation light spectrum of alizarin calculated from the estimated background light spectrum and the spectrum of the measurement light. In addition, FIGS. 13 and 15 illustrate the spectral characteristics of alizarin and indigo obtained in this example, and the spectral absorbances of alizarin and indigo obtained from a known database.

In FIGS. 12 and 14, the horizontal axis represents wavelength, and the vertical axis represents relative intensity. In FIGS. 13 and 15, the horizontal axis represents the wavelength, the left vertical axis represents the relative intensity of the spectral characteristic, and the right vertical axis represents the spectral absorbance (without scale). Furthermore, in FIGS. 12A and 14, a solid curve represents the measurement light spectrum, and a broken curve represents the background light spectrum. As is found from FIGS. 13 and 15, in the spectrums of alizarin and indigo obtained in this example, a steep peak as seen in the spectrum obtained from the database was not observed, but a peak was observed at a wavelength position corresponding to the peak of the spectrum obtained from the database. This result has suggested possibility of identification of alizarin and indigo using the spectral measurement device 100.

Third Example

Figure 16:
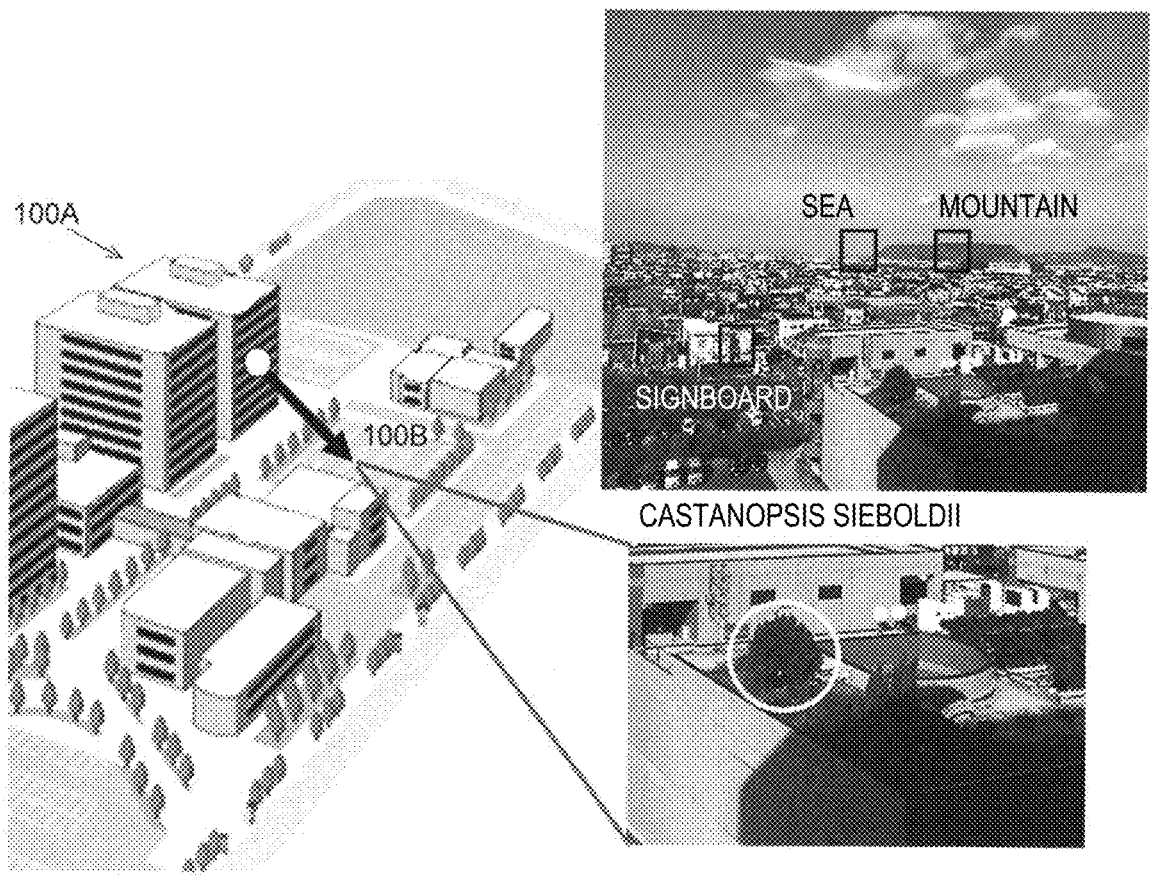
FIG. 16 is a view illustrating a model environment of Third Example with measuring a spectral characteristic of a distant measurement object using the spectral measurement device of the present embodiment.

Third Example is an example in which active spectroscopy of a measurement object is measured using the sun as a light source. In this example, the spectral measurement device 100 was provided in a room on the sixth floor of a building, and the spectral characteristic of the object visible from the window of the room was measured. Specifically, as illustrated in FIG. 16, a plant (*Castanopsis sieboldii*) on the roof of a two-story building 100B adjacent to a building 100A with the spectral measurement device 100 provided with a passage interposed between them, a red signboard located far from the building 100A, a blue sea, and a green mountain were set as measurement objects, and spectral characteristics of reflected light generated by irradiating these measurement objects with sunlight at a temperature of about 5000 Kelvin (K) were measured.

Figure 17:
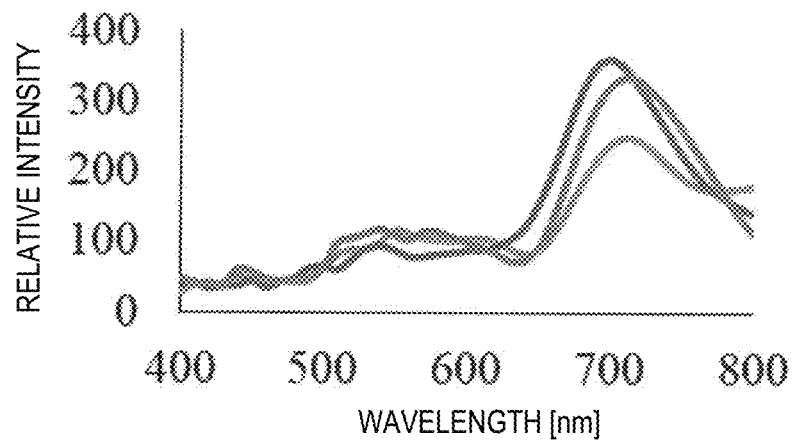
FIG. 17 is a graph illustrating a spectral characteristic of a tree (*Castanopsis sieboldii*).
Figure 18A:
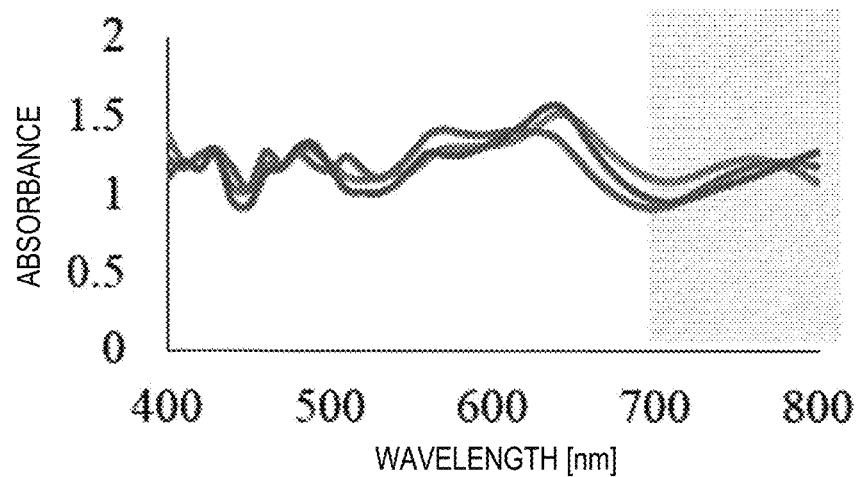
FIG. 18A is an absorption spectrum of a tree when a spectral characteristic of the sky is set to a background light spectrum.
Figure 18B:
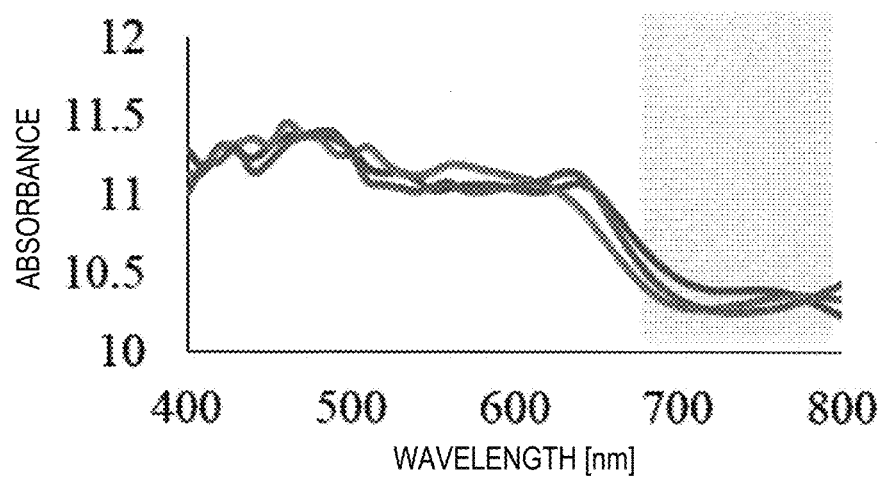
FIG. 18B is an absorption spectrum of a tree when a background light spectrum is estimated by the method of the present embodiment.

FIG. 17 illustrates a result of measuring spectral characteristics in a predetermined measurement range including the plant on the rooftop of the building 100B three times using the spectral measurement device 100. In addition, FIG. 18A illustrates an absorption spectrum of a plant calculated from the spectral characteristic illustrated in FIG. 17 and the background light spectrum which was the spectral characteristic of the sky, and FIG. 18B illustrates an absorption spectrum of a plant calculated from the spectral characteristic illustrated in FIG. 17 and the background light spectrum which was estimated as the spectral radiance spectrum of the black body fitted in an envelope shape on the upper side of the graph of the spectral characteristic illustrated in FIG. 17. Herein, the background light spectrum was estimated using the spectrum of the spectral radiance I of the black body when the temperature T was set to about 5000 Kelvin (K) in the formula (1).

As is found from the comparison between FIG. 18A and FIG. 18B, in the absorption spectrum illustrated in FIG. 18A, the change in absorbance in the wavelength range of 400 nm to 800 mn was small, but in the absorption spectrum shown in FIG. 18B, the absorbance on the long wavelength side (wavelength range of 700 to 800 nm) decreased. It is known that chlorophyll contained in the leaves of plants such as *Castanopsis sieboldii* does not absorb a wavelength of 700 to 800 nm, and thus the absorption spectrum illustrated in FIG. 18B can be said to be a characteristic waveform of a plant containing chlorophyll, and it has been suggested that this method is likely to be used to identify the presence of a plant in the measurement range.

Figure 19A:
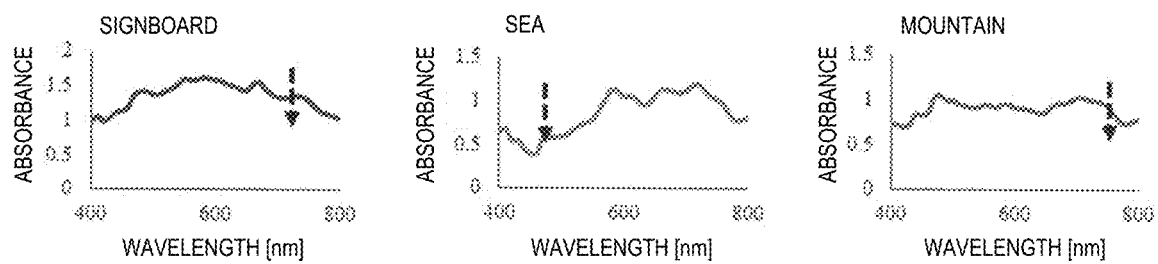
FIG. 19A illustrates Third Example, and absorption spectrums of a signboard, a sea, and a mountain when a spectral characteristic of the sky is set to a background light spectrum.
Figure 19B:
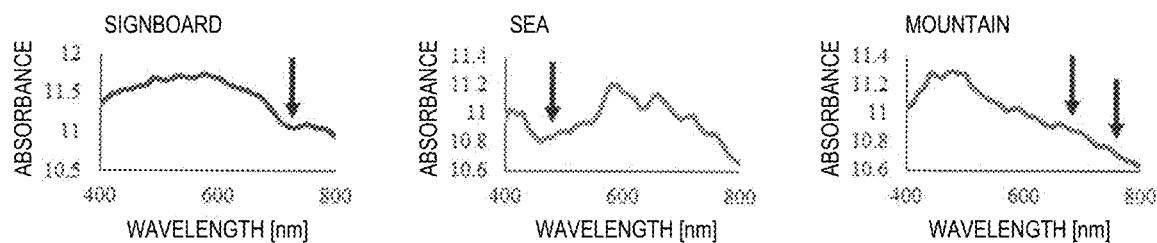
FIG. 19B illustrates Third Example, and absorption spectrums of a signboard, a sea, and a mountain when a background light spectrum is estimated by the method of the present embodiment.

In addition, FIG. 19A illustrates an absorption spectrum calculated from the spectral characteristic of the sky as a background light spectrum and the spectral characteristic obtained for the measurement range including each measurement object (signboard, sea, mountain), and FIG. 19B illustrates an absorption spectrum calculated from the background light spectrum and each spectral characteristic by estimating, as a background light spectrum, a spectral radiance spectrum of the black body fitted in an envelope shape on the upper side of the graph of the spectral characteristic obtained for the measurement range including each measurement object.

As is found from the comparison between FIG. 19A and FIG. 19B, the absorption spectrum illustrated in FIG. 19B has the significantly decreased absorbance (the portion indicated by the downward arrow in each graph) in the wavelength range corresponding to the color of each measurement object, as compared with the absorption spectrum illustrated in FIG. 19A. The above-described result has suggested possibility of identification by color of the measurement object located far from the spectral measurement device 100.

Fourth Example

Fourth Example is an example of measuring the passive spectral characteristic of light (radiation light) emitted from the wrist and the back of the hand of a subject (human). The radiation light (measurement light) emitted from the wrist and the back of the hand of the subject (human) includes radiation light emitted from the skin of the wrist or the back of the hand and radiation light emitted from a blood vessel passing through the wrist or the back of the hand. The spectral characteristic of the radiation light emitted from the skin of the wrist or the back of the hand involves the information on the skin, and the spectral characteristic of the radiation light emitted from the blood vessel passing through the wrist or the back of the hand involves the information on the blood flowing in the blood vessel. That is, the measurement light emitted from the wrist and the back of the hand is separated into the radiation light emitted from the skin and the radiation light emitted from the blood vessel, and the respective spectral characteristics are measured, so that the information on the skin and the information on the blood can be acquired from the respective spectral characteristics. When the information on the skin is acquired, the radiation light emitted from the blood vessel is the background light, and when the information on the blood is acquired, the radiation light emitted from the skin is the background light.

However, actually, the above-described measurement light cannot be separated into the radiation light emitted from the skin of the wrist or the back of the hand and the radiation light emitted from the blood vessel. Therefore, the spectral characteristic of the background light is estimated from the spectral radiance I ($\lambda$, T) of the black body represented by the above formula (1). Hereinafter, a case where a blood glucose level is acquired as information on blood will be described. In this example, in order to relatively increase the emission intensity of the radiation light emitted from the skin of the wrist or the back of the hand, the radiation light was measured in a state where a conjugate plane lattice 73 of the spectral measurement device 100 was heated and maintained at about 60° C.

First, the spectral measurement device 100 was used to actually measure the spectral characteristics of the black body heated to a temperature around the body temperature of the subject (36° C. to 37° C.), and the measured values (actual measured values) were used to determine the spectral sensitivity coefficient Sp of the spectral measurement device 100. Then, the spectral characteristic of radiation light (that is, the measurement light) emitted from the wrist and the back of the hand of the subject was measured using the spectral measurement device 100. After the spectral characteristic of the measurement light is measured, the processing unit 504 fits a value obtained by multiplying the thermal radiation spectrum of the black body at the temperature around the body temperature of the subject by the spectral sensitivity coefficient Sp to the graph (spectrum) of the spectral characteristic of the measurement light to estimate the graph (spectrum) of the spectral characteristic of the radiation light (background light) emitted from the skin, and uses the difference between the estimated spectrum and the measurement light spectrum to determine the spectrum of the radiation light emitted from the blood vessel which is the measurement object. The spectral characteristic of the radiation light emitted from the blood vessel is a passive spectral characteristic, and thus in Fourth Example, a value obtained by multiplying the thermal radiation spectrum of the black body by the spectral sensitivity coefficient Sp was fitted in an envelope shape on the lower side of the spectral characteristic of the measurement light.

After the spectrum of the radiation light emitted from the blood vessel is obtained, the processing unit 504 calculates the blood glucose level of the subject on a basis of the correlation between this spectrum and the blood glucose level. Therefore, the processing unit 504 corresponds to a blood glucose level calculation unit. Examples of the correlation between the spectrum and the blood glucose level include: a formula for calculating the blood glucose level from a peak intensity value specific to the blood glucose level found in the spectrum; and a graph and a table indicating the relationship between the peak intensity value and the blood glucose level. The correlation between the spectrum and the blood glucose level is previously stored in the storage unit 501.

Figure 20A:
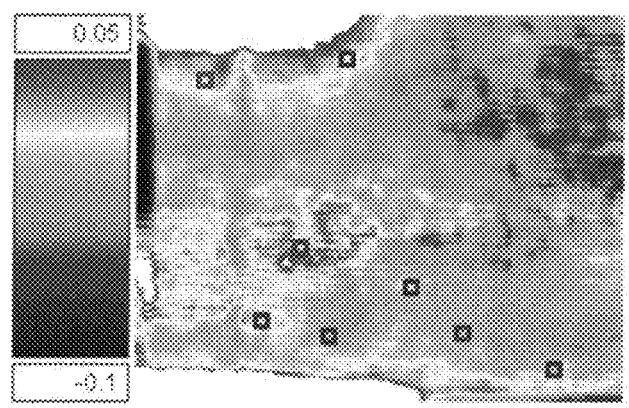
FIG. 20AA is a pseudo color image of the left wrist of a subject 1 in Fourth Example with measuring a spectral characteristic of a measurement object (blood vessel) using the spectral measurement device of the present embodiment, and FIG. 20AB is a graph illustrating an integrated spectrum of the blood vessel obtained from the spectral characteristic of the radiation light at a plurality of points on the left wrist and an absorption spectrum of standard blood.
Figure 20A:
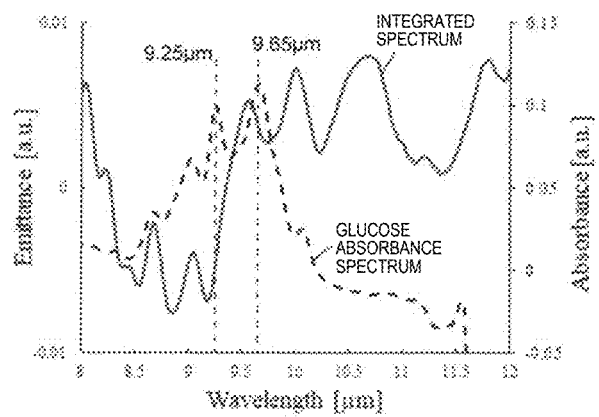
Figure 20B:
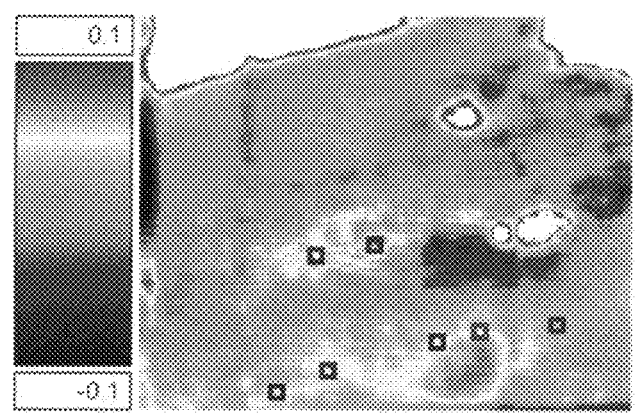
FIG. 20BA is a pseudo color image of the back of the left hand of the subject 1, and FIG. 20BB is a graph illustrating an integrated spectrum of the blood vessel obtained from spectral characteristics of radiation light at a plurality of positions on the back of the left hand and a standard absorption spectrum of blood, in Fourth Example with measuring the spectral characteristic of the measurement object (blood vessel) using the spectral measurement device of the present embodiment.
Figure 20B:
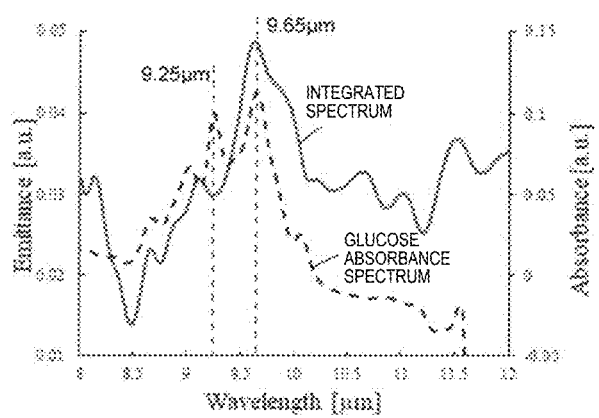
Figure 21A:
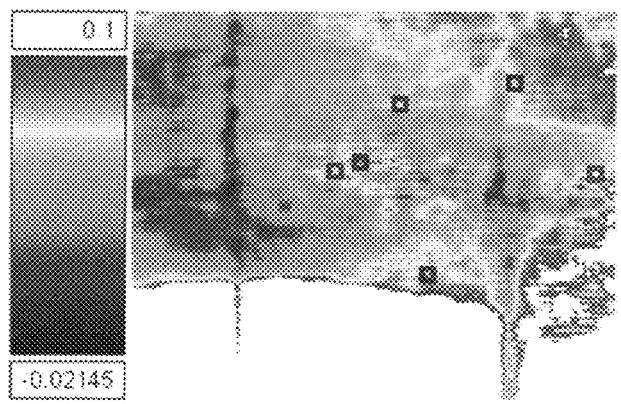
FIG. 21AA is a pseudo color image of the left wrist of a subject 2 in Fourth Example with measuring a spectral characteristic of a measurement object (blood vessel) using the spectral measurement device of the present embodiment, and FIG. 21AB is a graph illustrating an integrated spectrum of the blood vessel obtained from the spectral characteristic of the radiation light at a plurality of points on the left wrist and an absorption spectrum of standard blood.
Figure 21A:
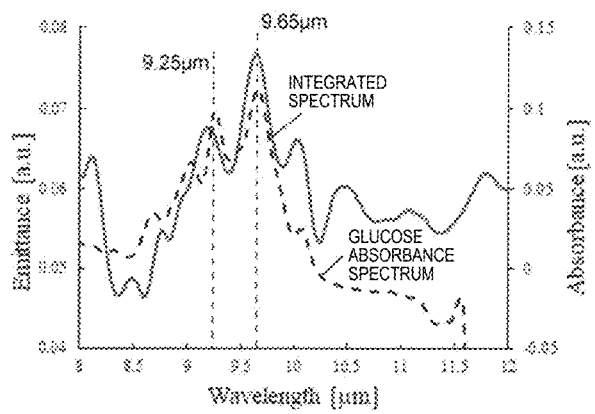
Figure 21B:
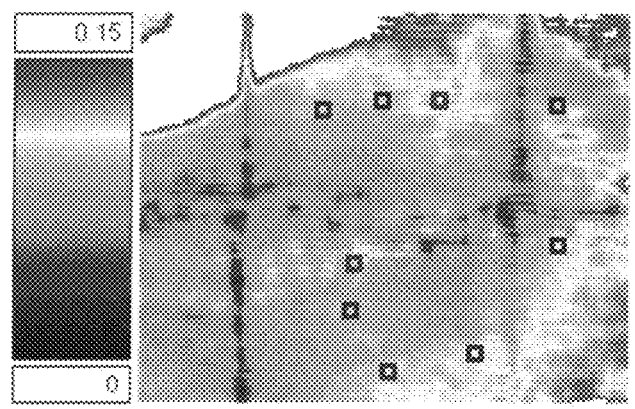
FIG. 21BA is a pseudo color image of the back of the left hand of the subject 2, and FIG. 21BB is a graph illustrating an integrated spectrum of the blood vessel obtained from spectral characteristics of radiation light at a plurality of positions on the back of the left hand and a standard absorption spectrum of blood, in Fourth Example with measuring the spectral characteristic of the measurement object (blood vessel) using the spectral measurement device of the present embodiment.
Figure 21B:
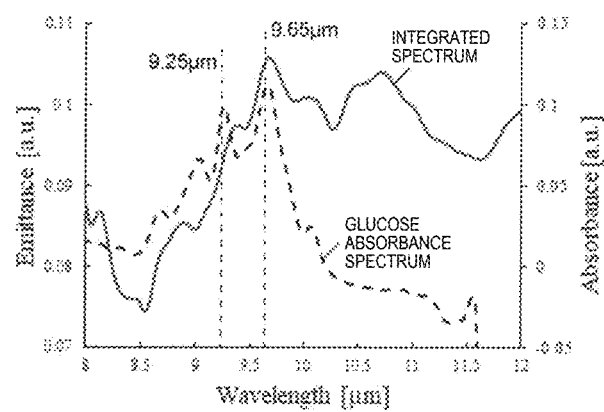

The results of measuring blood glucose levels of two subjects (hereinafter referred to as subject 1 and subject 2) by the method described above will be described. FIGS. 20A and 20B illustrate the measurement result of the subject 1, and FIGS. 21A and 21B illustrate the measurement result of the subject 2.

FIG. 20AA and FIG. 20BA illustrate pseudo color images obtained by visualizing the degree of emission of the radiation light at the wrist and the back of the hand of the subject 1 based on the degree of emission at 9.65 µm, which is one of the absorption wavelengths of glucose. FIG. 20AA and FIG. 20BA are actually color images, but they are represented in black and white herein. In the above pseudo color image, colors are painted in 10 stages according to the magnitude of the emission degree, and in the actual image, the maximum value and the minimum value of the emission degree are represented by red and dark blue, respectively. In the wrist and the back of the hand, the region where the blood vessel exists near the skin has a higher temperature than other regions, and has a higher degree of emission of the radiation light. Therefore, the region where the blood vessel is located can be specified from the color of the pseudo color image in FIGS. 20AA and 20BA, and the blood glucose level can be obtained from the spectrum of the radiation light emitted from the region.

The graph indicated by a solid line in FIG. 20AB is a graph obtained by integrating spectrums of radiation light emitted from 8 points marked with a square in the pseudo color image of the wrist in FIG. 20AA, and the graph indicated by a solid line in FIG. 20BA is a graph obtained by integrating spectrums of radiation light emitted from 7 points marked with a square in the pseudo color image of the back of the hand in of FIG. 20BA (hereinafter, referred to as integrated spectrum). In addition, the graphs indicated by broken lines in FIGS. 20AB and FIG. 20BB are graphs obtained by vertically inverting the absorption spectrum of a standard human blood glucose level acquired from a known database.

In the subject 2, similarly to the subject 1, there were obtained a pseudo color image of the wrist and the back of the hand and an integrated spectrum of radiation light emitted from the blood vessel in the wrist and the back of the hand. FIGS. 21AA and 21AB and FIGS. 21BA and 21BB illustrate these results. In FIGS. 20AB and 20BB and FIGS. 21AB and 21BB, the horizontal axis represents the wavelength (µm), the left vertical axis represents the relative intensity of the integrated spectrum of the radiation light, and the right vertical axis represents the spectral absorbance.

As is found from FIGS. 20AB and 20BB and FIGS. 21AB and 21BB, in the integrated spectrum of the radiation light, there was observed at least an emission peak corresponding to an absorption peak specific to glucose observed at wavelengths of 9.25 µm and 9.65 µm of the absorption spectrum acquired from the database. In particular, in the integrated spectrums of the radiation light illustrated in FIGS. 20BB and 21AB, the peak position and the peak waveform were similar to those of the absorption spectrum acquired from the database, and these spectrums were used to calculate the blood glucose level on the basis of the correlation between the emission spectrum and the blood glucose level. As a result, the blood glucose level of the subject 1 was 111 mg/dL, and the blood glucose level of the subject 2 was 112 mg/dL. This result has suggested possibility of measurement of the blood glucose level using the spectral measurement device 100 by setting measurement point appropriately.

As described above, in the above embodiment, the spectral characteristic of the background light is estimated using the spectral radiance of the black body. The spectral radiance of the black body can be represented by a mathematical formula known as a function of temperature and wavelength according to Planck's law, and thus the spectral characteristic information on the background light can be easily set.

However, if the type or the wavelength range of the light incident on the measurement object is known, the spectral characteristic of the background light may be estimated using the spectral characteristic of the known light. In addition, it is expected that the spectral characteristic of the background light varies every time the spectral characteristic of the light emitted from the measurement object is measured. In addition, the intensity of the background light varies depending on the absorption characteristic and a reflection characteristic of an object present around the measurement object. Therefore, every time the spectral characteristic of the measurement object is measured, the spectral measurement device 100 is used to obtain the spectral characteristic of the light emitted from the environment similar to the surroundings of the measurement object without including the measurement object, and this obtained spectral characteristic may be used as the spectral characteristic of the background light.

In addition, the phase shifter is not limited to the configuration described in the above embodiment, and a Michelson interferometer can be used.

REFERENCE SIGNS LIST

100 . . . Spectral Measurement Device
110 . . . Measurement Light
10 . . . Housing
101 . . . First Housing
102 . . . Second Housing
20 . . . Phase Shifter
40 . . . Detector
50 . . . Control Device
501 . . . Storage Unit
503 . . . Background Light Information Storage Unit
504 . . . Processing Unit
505 . . . Communication Unit

The invention claimed is:

1. A spectral measurement device configured to detect measurement light including light emitted from a measurement object and to measure a spectral characteristic of the light emitted from the measurement object from a result of the detection, the spectral measurement device comprising:
a spectral optical system configured to disperse the measurement light;
a detection unit configured to detect intensity of the measurement light dispersed by the spectral optical system;
a spectral characteristic acquisition unit configured to acquire a measurement light spectral characteristic indicating a relationship between a light intensity and a wavelength of the measurement light on a basis of a detection result of the detection unit;
a storage unit configured to store spectral characteristic information on possible background light, the information indicating a spectral characteristic of the possible background light, which involves a spectral sensitivity characteristic of an optical path of measurement light from the spectral optical system to the detection unit; and
a processing unit configured to obtain a spectral characteristic of background light which is light emitted from an ambience of the measurement object, from the measurement light spectral characteristic and the spectral characteristic information on the possible background light.

2. The spectral measurement device according to claim 1, wherein the spectral characteristic information on the possible background light includes information which involves the spectral sensitivity characteristic and indicates a relationship between spectral radiance of sunlight and a wavelength.

3. The spectral measurement device according to claim 1, wherein the spectral characteristic information on the possible background light includes information which involves the spectral sensitivity characteristic and indicates a relationship between spectral radiance of a black body and a wavelength.

4. The spectral measurement device according to claim 1, wherein
the spectral characteristic information on the possible background light includes a plurality of types of possible background light spectral characteristics which are spectral characteristics of possible background light, involving the spectral sensitivity characteristic, and
the processing unit is configured to perform fitting process on the measurement light spectral characteristic to extract the spectral characteristic of the background light from among spectral characteristics of the plurality of types of possible background light.

5. The spectral measurement device according to claim 1, wherein
the spectral characteristic information on the possible background light includes possible background light spectral characteristic which are spectral characteristics of possible background light, involving the spectral sensitivity characteristic at a plurality of temperatures, and
the processing unit is configured to perform fitting process on the measurement light spectral characteristic to extract the spectral characteristic of the background light from among possible background light spectral characteristics at the plurality of temperatures.

6. The spectral measurement device according to claim 1, wherein the processing unit is configured to calculate a spectral characteristic of light emitted from the measurement object from a difference between the measurement light spectral characteristic and the background light spectral characteristic.

7. The spectral measurement device according to claim 6, wherein
the measurement object is a blood vessel of a subject, and
the device further comprises a blood glucose level calculation unit configured to calculate a blood glucose level of the subject on a basis of a correlation between a spectral characteristic of light emitted from the measurement object and a blood glucose level.

8. A spectral measurement method for detecting measurement light including light emitted from a measurement object by a detection unit and measuring a spectral characteristic of the light emitted from the measurement object from the detection result, the spectral measurement method comprising:
- a step of dispersing the measurement light by a spectral optical system;
- a step of acquiring a spectral characteristic of the measurement light dispersed by the spectral optical system; and
- a step of obtaining a spectral characteristic of background light which is light emitted from an ambience of the measurement object, from a measurement light spectral characteristic and spectral characteristic information on possible background light, the information indicating a spectral characteristic of the possible background light, which involves a spectral sensitivity characteristic of an optical path of the measurement light from the spectral optical system to the detection unit.

9. The spectral measurement method according to claim 8, wherein the spectral characteristic information on the possible background light includes information which involves the spectral sensitivity characteristic and indicates a relationship between spectral radiance of sunlight and a wavelength.

10. The spectral measurement method according to claim 8, wherein the spectral characteristic information on the possible background light includes information which involves the spectral sensitivity characteristic and indicates a relationship between spectral radiance of a black body and a wavelength.

11. The spectral measurement method according to claim 8, wherein
the spectral characteristic information on the possible background light includes a plurality of types of possible background light spectral characteristics which are spectral characteristics of possible background light, involving the spectral sensitivity characteristic, and
a step of obtaining the spectral characteristic of the background light uses fitting process on the spectral characteristic of the measurement light to extract the spectral characteristic of the background light from the plurality of types of possible background light spectral characteristics.

12. The spectral measurement method according to claim 8, wherein
the spectral characteristic information on the possible background light includes possible background light spectral characteristics which are spectral characteristics of possible background light, involving the spectral sensitivity characteristic at a plurality of temperatures, and
a step of obtaining the spectral characteristic of the background light uses fitting process on the spectral characteristic of the measurement light to extract the spectral characteristic of the background light from possible background light spectral characteristics at the plurality of temperatures.

13. The spectral measurement method according to claim 8, further comprising:
- a step of calculating a spectral characteristic of light emitted from the measurement object from a difference between the measurement light spectral characteristic and the background light spectral characteristic.

14. The spectral measurement method according to claim 13, wherein
the measurement object is a blood vessel of a subject, and
the method further comprises a step of calculating a blood glucose level of the subject on a basis of a correlation between a spectral characteristic of light emitted from the measurement object and a blood glucose level.

* * * * *